US011147611B2

(12) United States Patent
Kawashima

(10) Patent No.: US 11,147,611 B2
(45) Date of Patent: Oct. 19, 2021

(54) RELAY DEVICE AND ULTRASONIC-SURGICAL AND ELECTROSURGICAL SYSTEM

(71) Applicant: OLYMPUS CORPORATION, Tokyo (JP)

(72) Inventor: Ko Kawashima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1109 days.

(21) Appl. No.: 15/667,871

(22) Filed: Aug. 3, 2017

(65) Prior Publication Data
US 2017/0325838 A1 Nov. 16, 2017

Related U.S. Application Data

(63) Continuation of application No. 12/357,512, filed on Jan. 22, 2009, now Pat. No. 9,757,142, which is a
(Continued)

(51) Int. Cl.
*A61B 18/14* (2006.01)
*A61B 18/12* (2006.01)
(Continued)

(52) U.S. Cl.
CPC ...... *A61B 18/14* (2013.01); *A61B 17/320092* (2013.01); *A61B 18/1206* (2013.01);
(Continued)

(58) Field of Classification Search
CPC .............. A61B 18/1206; A61B 18/14; A61B 2017/320093; A61B 2017/320095; A61B 2018/1273; A61B 2018/128; A61N 7/02
See application file for complete search history.

(56) References Cited

U.S. PATENT DOCUMENTS 5,015,227 A 5/1991 Broadwin et al.
5,575,789 A 11/1996 Bell et al.
(Continued)

FOREIGN PATENT DOCUMENTS

JP H03-151957 A 6/1991
JP H06-042893 B2 6/1994
(Continued)

OTHER PUBLICATIONS

Non Final Office Action dated Oct. 8, 2009 received in U.S. Appl. No. 12/357,512.
(Continued)

*Primary Examiner* — Michael F Peffley
*Assistant Examiner* — Samantha M Good
(74) *Attorney, Agent, or Firm* — Scully, Scott, Murphy & Presser, P.C.

(57) ABSTRACT

A surgical controller for controlling a treatment instrument, the surgical controller including one or more processors configured to: detect whether a switch is actuated; control a first surgical energy source to actuate the treatment instrument to perform a first treatment based on a first surgical energy in response to detecting that the switch is actuated; detect whether a parameter reaches a predetermined value during actuation of the treatment instrument to perform the first treatment; and control the second surgical energy source to actuate the treatment instrument to perform a second treatment based on a second surgical energy different from the first surgical energy in response to detecting that the parameter reached the predetermined value.

10 Claims, 25 Drawing Sheets

Related U.S. Application Data continuation-in-part of application No. 11/501,357, filed on Aug. 9, 2006, now abandoned.

(51) Int. Cl.
*A61B 17/32* (2006.01)
*A61B 17/00* (2006.01)
*A61N 7/02* (2006.01)

(52) U.S. Cl.
CPC ............... *A61B 18/1445* (2013.01); *A61B 2017/00017* (2013.01); *A61B 2017/00106* (2013.01); *A61B 2017/00154* (2013.01); *A61B 2017/00199* (2013.01); *A61B 2017/00212* (2013.01); *A61B 2017/320093* (2017.08); *A61B 2017/320095* (2017.08); *A61N 7/02* (2013.01)

(56) References Cited

U.S. PATENT DOCUMENTS

| | | | |
|---|---|---|---|
| 5,836,897 | A | 11/1998 | Sakurai et al. |
| 6,383,183 | B1 * | 5/2002 | Sekino ............... A61B 18/1206 606/34 |
| 6,623,423 | B2 | 9/2003 | Sakurai et al. |
| 6,666,860 | B1 | 12/2003 | Takahashi |
| 6,669,690 | B1 | 12/2003 | Okada et al. |
| 7,063,692 | B2 | 6/2006 | Sakurai et al. |
| 7,353,068 | B2 | 4/2008 | Tanaka et al. |
| 2004/0019347 | A1 | 1/2004 | Sakurai et al. |
| 2004/0097916 | A1 | 5/2004 | Thompson et al. |
| 2008/0125768 | A1 | 5/2008 | Tahara et al. |
| 2009/0131929 | A1 | 5/2009 | Shimizu |

FOREIGN PATENT DOCUMENTS

| | | |
|---|---|---|
| JP | 2000-271140 A | 10/2000 |
| JP | 2002-238919 A | 8/2002 |
| JP | 2003-033369 A | 2/2003 |
| JP | 2005-028168 A | 2/2005 |
| JP | 2006-081665 A | 3/2006 |
| JP | 2006-187668 A | 7/2006 |

OTHER PUBLICATIONS

Non Final Office Action dated Oct. 4, 2013 received in U.S. Appl. No. 12/357,512.
Non Final Office Action dated Apr. 12, 2016 received in U.S. Appl. No. 12/357,512.
Non Final Office Action dated Jul. 22, 2009 received in U.S. Appl. No. 11/501,357.
Non Final Office Action dated May 13, 2014 received in U.S. Appl. No. 11/501,357.
Final Office Action dated Dec. 30, 2016 received in U.S. Appl. No. 12/357,512.
Final Office Action dated Apr. 20, 2010 received in U.S. Appl. No. 12/357,512.
Final Office Action dated Mar. 21, 2014 received in U.S. Appl. No. 12/357,512.
Final Office Action dated Dec. 18, 2014 received in U.S. Appl. No. 11/501,357.
Final Office Action dated Jan. 14, 2010 received in U.S. Appl. No. 11/501,357.
Japanese Office Action dated Oct. 6, 2009 in Japanese Patent Application No. 2007-065551.

* cited by examiner

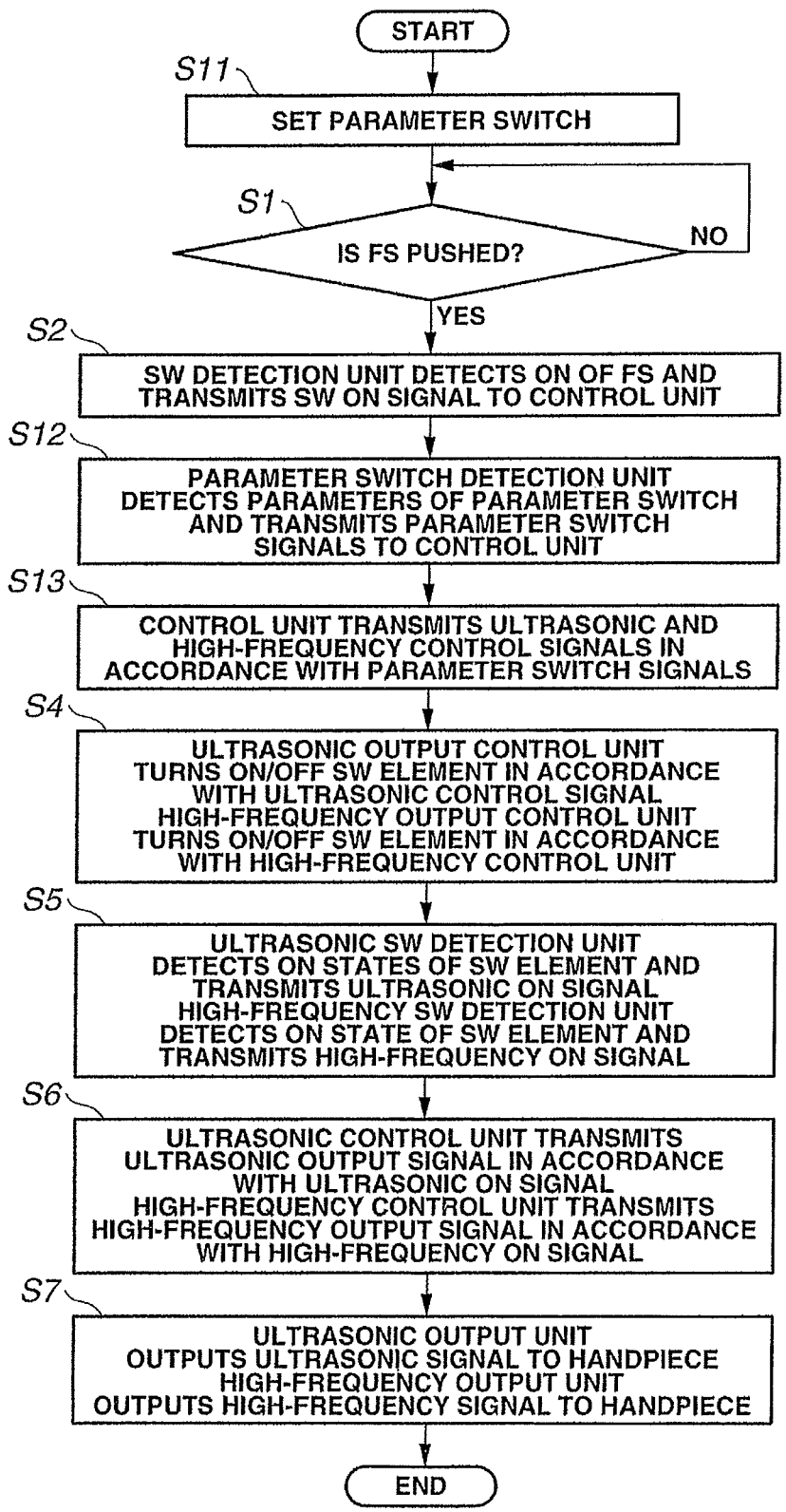

RELAY DEVICE AND ULTRASONIC-SURGICAL AND ELECTROSURGICAL SYSTEM

CROSS REFERENCES TO RELATED APPLICATIONS

This application is a continuation application of U.S. patent application Ser. No. 12/357,512, filed on Jan. 22, 2009 and issued as U.S. Pat. No. 9,757,142 B2 on Sep. 12, 2017, which is a continuation-in-part of U.S. patent application Ser. No. 11/501,357 filed on Aug. 9, 2006 and now abandoned, the entire contents of each of which are incorporated herein by reference.

BACKGROUND OF THE INVENTION

1. Field of the Invention

The present invention relates to a relay device connected to an ultrasonic surgical device and an electrosurgical device and an ultrasonic-surgical and electrosurgical system including the relay device.

2. Description of the Related Art

Conventionally, surgeries use surgical devices including various handpieces, such as an ultrasonic scalpel and an electric scalpel, for use in tissue ablation and simultaneous hemostasis.

An ultrasonic surgical device and an electrosurgical device, serving as surgical devices, are individually operated. An operator has to manipulate switches dedicated to the respective devices to control the devices and operate handpieces connected to the devices.

Under the above-described circumstances, as the number of surgical devices increases, the operator's manipulation becomes more complicated. Unfortunately, changing a handpiece to another one results in an increase in time required for surgery.

Japanese Examined Patent Application Publication No. 6-42893 discloses a surgical system capable of ultrasonically disintegrating tissue and simultaneously allowing an electrosurgical device to supply high-frequency energy to the handpiece of the ultrasonic surgical device. This surgical system can simultaneously output ultrasonic vibration and high-frequency current.

Japanese Unexamined Patent Application Publication No. 2003-33369 discloses a surgical system including means for controlling the rate of high-frequency current output to ultrasonic vibration output. This system does not need to control the respective outputs.

SUMMARY OF THE INVENTION

A surgical controller for controlling a treatment instrument, the surgical controller comprising one or more processors configured to: detect whether a switch is actuated; control a first surgical energy source to actuate the treatment instrument to perform a first treatment based on a first surgical energy in response to detecting that the switch is actuated; detect whether a parameter reaches a predetermined value during actuation of the treatment instrument to perform the first treatment; and control the second surgical energy source to actuate the treatment instrument to perform a second treatment based on a second surgical energy different from the first surgical energy in response to detecting that the parameter reached the predetermined value.

A method for controlling a treatment instrument to perform a treatment, the method comprising: detecting whether a switch is actuated; controlling a first surgical energy source to actuate the treatment instrument to perform a first treatment based on a first surgical energy in response to detecting that the switch is actuated; detecting whether a parameter reaches a predetermined value during actuation of the treatment instrument to perform the first treatment; and controlling the second surgical energy source to actuate the treatment instrument to perform a second treatment based on a second surgical energy different from the first surgical energy in response to detecting that the parameter reached the predetermined value.

A surgical apparatus comprising: a treatment instrument; and a surgical controller comprising one or more processors configured to: detect whether a switch is actuated; control a first surgical energy source to actuate the treatment instrument to perform a first treatment based on a first surgical energy in response to detecting that the switch is actuated; detect whether a parameter reaches a predetermined value during actuation of the treatment instrument to perform the first treatment; and control the second surgical energy source to actuate the treatment instrument to perform a second treatment based on a second surgical energy different from the first surgical energy in response to detecting that the parameter reached the predetermined value.

A surgical apparatus comprising: a treatment instrument; a switch; and a circuit configured to form a first electric connection between the switch and a surgical controller, a second electric connection between the treatment instrument and the surgical controller, and a third electric connection between the treatment instrument and the surgical controller, wherein the circuit is configured to: communicate with the surgical controller through the first electric connection in response to an occurrence that the switch is actuated; receive a first electric power from a first surgical energy source through the second electric connection, wherein the first electric power is configured to actuate the treatment instrument to perform a first treatment based on a first surgical energy in response to the occurrence; and subsequent to receiving the first electric power, receive a second electric power from a second surgical energy source through the third electric connection, wherein the second electric power is configured to actuate the treatment instrument to perform a second treatment based on a second surgical energy in response to another occurrence that a parameter reached a predetermined value during actuation of the treatment instrument to perform the first treatment.

BRIEF DESCRIPTION OF THE DRAWINGS

FIG. 13 is a flowchart of the operation of an ultrasonic-surgical and electrosurgical system according to the second embodiment;

DETAILED DESCRIPTION OF THE PREFERRED EMBODIMENTS

First Embodiment

A first embodiment of the present invention will now be described with reference to FIGS. 1 to 9.

Figure 1:
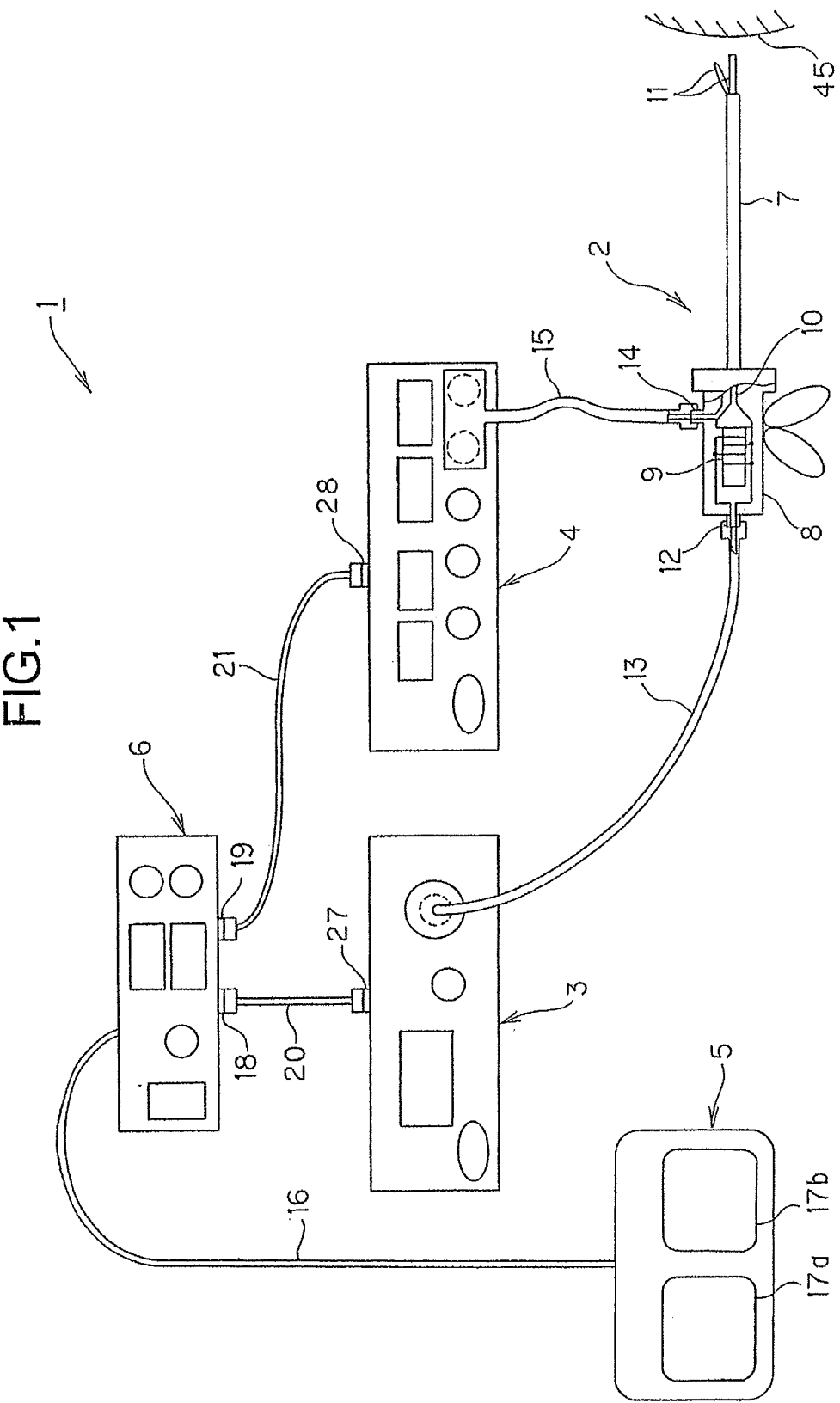
FIG. 1 is an external view showing a structure of an ultrasonic-surgical and electrosurgical system including a relay device according to a first embodiment of the present invention.

FIG. 1 shows a structure of an ultrasonic-surgical and electrosurgical system including a relay device according to a first embodiment of the present invention. It is an object of the present invention to provide a relay device that is applicable in the use of an existing ultrasonic surgical device and an existing electrosurgical device and is capable of improving the operability of the devices, and an ultrasonic surgical and electrosurgical system including the relay device.

More specifically, the relay device according to the present invention is capable of controlling at least one of an output timing and an output mode of each of the ultrasonic surgical device and the electrosurgical device through a single switch unit or element.

Referring to FIG. 1, an ultrasonic-surgical and electrosurgical system 1 according to the first embodiment of the present invention includes a handpiece 2, an ultrasonic surgical device 3, an electrosurgical device 4, a footswitch 5, and a relay device 6. The handpiece 2 functions as an ultrasonic/high-frequency treatment instrument for treatment using ultrasonic vibration and high-frequency current (or high-frequency signal) on biological tissue 45. The ultrasonic surgical device 3 supplies an ultrasonic signal as a driving signal (driving power) for driving of the handpiece 2. The electrosurgical device 4 supplies a high-frequency signal as a driving signal (driving power) for driving of the handpiece 2. The footswitch 5 serves as a switch unit for the ON/OFF operation or the like of power supply. The relay device 6 controls output modes and output timings of the ultrasonic surgical device 3 and the electrosurgical device 4.

The handpiece 2 has an elongated sheath 7. The proximal end of the sheath 7 is provided with a handpiece body 8 which an operator holds during a treatment.

The handpiece body 8 includes an ultrasonic transducer 9 connected to the proximal end of an ultrasonic transmitting member 10, which is inserted through the sheath 7.

The distal end of the ultrasonic transmitting member 10 protrudes from the distal end of the sheath 7 and serves as a stationary segment of a treatment section 11 for treatment using ultrasonic vibrations. The treatment section 11 is also used for treatment section using a high-frequency signal, which will be described later.

The back end of the handpiece body 8 is provided with an ultrasonic connector 12. The ultrasonic connector 12 is connected to the ultrasonic transducer 9. The ultrasonic connector 12 is also connected to an output connector of the ultrasonic surgical device 3 via an ultrasonic handpiece cable 13. The ultrasonic handpiece cable 13 is detachably connected to the ultrasonic connector 12.

The ultrasonic surgical device 3 supplies an ultrasonic signal, serving as a driving signal, to the ultrasonic transducer 9 through the ultrasonic handpiece cable 13, thus vibrating the ultrasonic transducer 9. The ultrasonic vibration is transmitted through the ultrasonic transmitting member 10 to the treatment section 11 at the distal end of the member 10.

Then, the operator can incise and coagulate the biological tissue 45 using ultrasonic vibration at the treatment section 11.

The handpiece body 8 further includes a handle. The operator can open and close a movable segment of the treatment section 11 by manipulating the handle.

The handpiece body 8 has a high-frequency connector 14. The high-frequency connector 14 is electrically connected to the ultrasonic transmitting member 10. The high-frequency connector 14 is also connected to an output connector of the electrosurgical device 4 via a high-frequency handpiece cable 15. The high-frequency handpiece cable 15 is detachably connected to the high-frequency connector 14.

The electrosurgical device 4 supplies a high-frequency signal (specifically, electrosurgical current) to the ultrasonic transmitting member 10 through the high-frequency handpiece cable 15. The electrosurgical current is transmitted through the treatment section 11 at the distal end of the ultrasonic transmitting member 10 to the biological tissue 45, which is in contact with the treatment section 11.

In the use of the handpiece 2 in FIG. 1, electrosurgical current flows between the stationary segment and the movable segment of the treatment section 11 through the biological tissue 45 in a bipolar manner. A monopolar handpiece 2' (refer to FIG. 19) may be used. In this case, electrosurgical current flows from the stationary segment of the treatment section 11 to a grounding pad (feedback electrode) through the biological tissue 45.

The footswitch 5 is connected to the relay device 6 through a footswitch cable 16. The footswitch 5 includes two pedal switches 17a and 17b, serving as switch elements.

The relay device 6 detects the ON/OFF operation performed by the operator through the pedal switches 17a and 17b. The relay device 6 has an ultrasonic connector 18 for ultrasonic power supply and a high-frequency connector 19 for high-frequency power supply. An ultrasonic surgical device connecting cable 20 and an electrosurgical device connecting cable 21 are connected to the ultrasonic and high-frequency connectors 18 and 19, respectively. The relay device 6 is connected to the ultrasonic surgical device 3 and the electrosurgical device 4 through the ultrasonic surgical device connecting cable 20 and electrosurgical device connecting cable 21, respectively.

Figure 2:
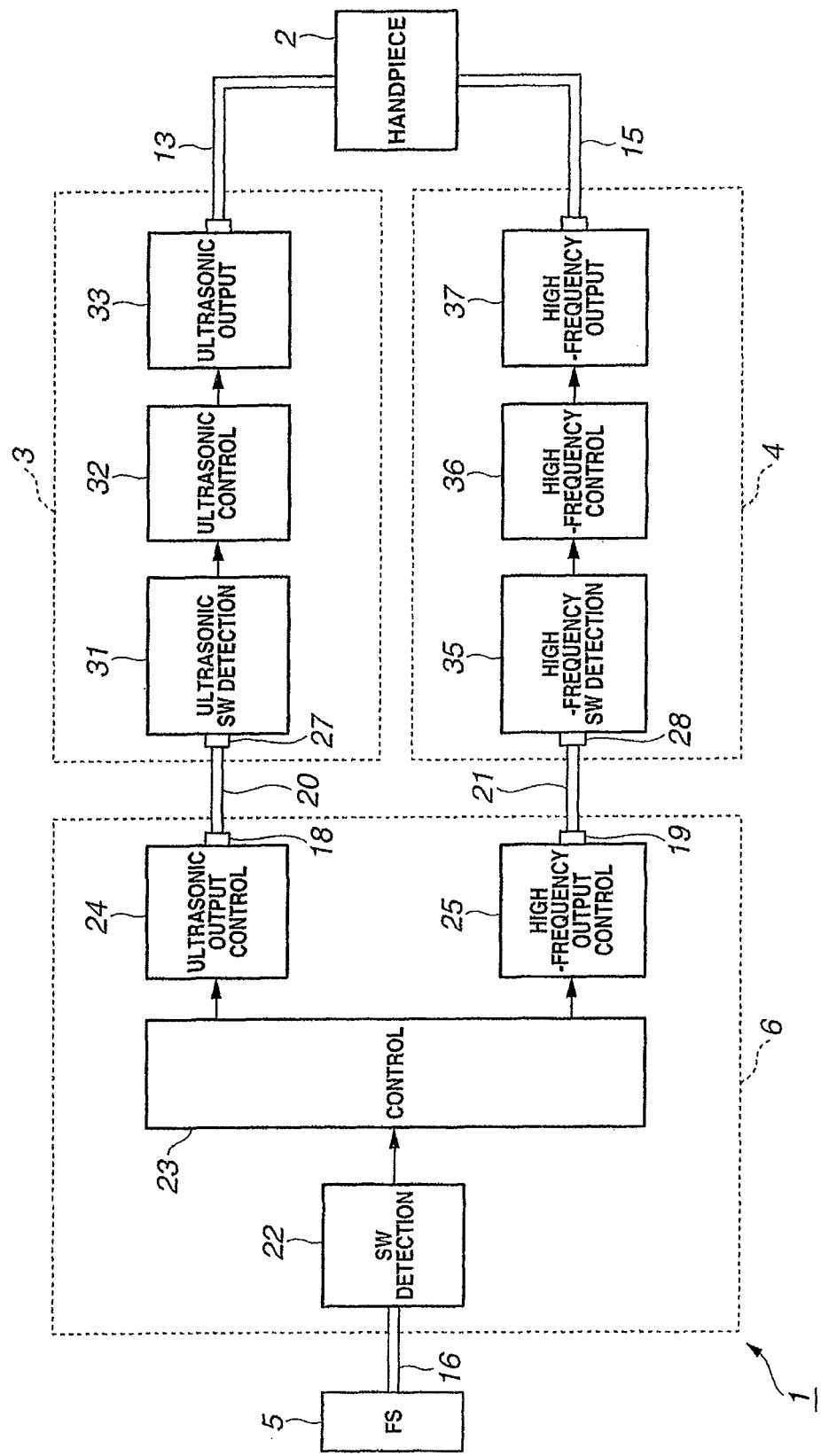
FIG. 2 is a block diagram illustrating the internal structure of the ultrasonic-surgical and electrosurgical system.

FIG. 2 shows entire internal structure of the ultrasonic-surgical and electrosurgical system 1. And, FIG. 3 shows the internal structure of the relay device 6.

Figure 3:
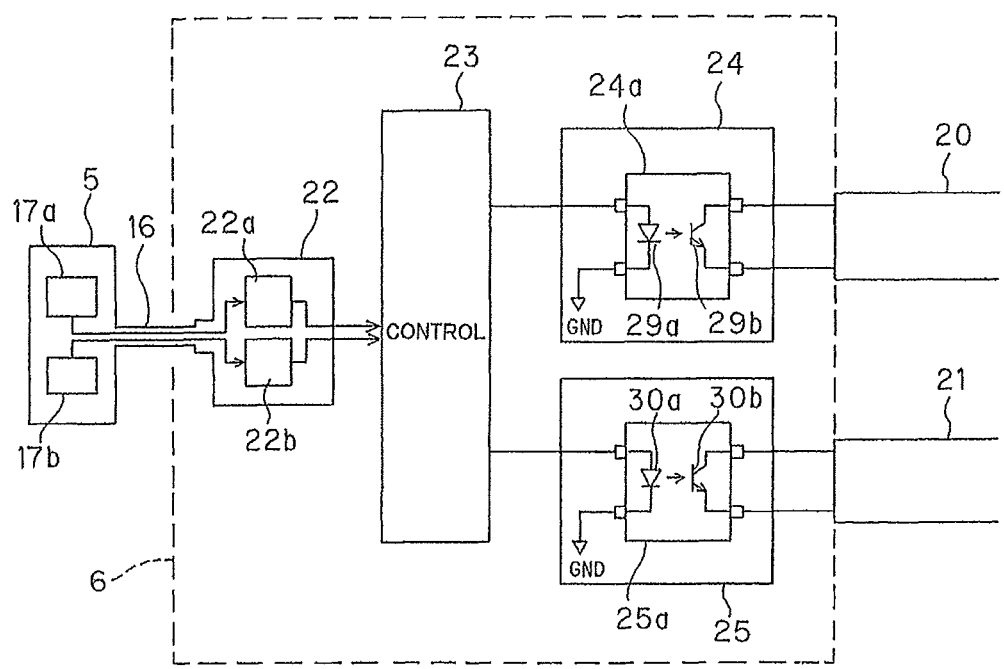
FIG. 3 is a block diagram showing the internal structure of the relay device.

Referring to FIGS. 2 and 3, the relay device 6 includes a switch (SW) detection unit 22 and a control unit 23. The switch detection unit 22 detects the turn-on/off of the footswitch 5. The control unit 23 controls the output modes and output timings of the ultrasonic surgical device 3 and the electrosurgical device 4 on the basis of an output signal of the switch detection unit 22.

As shown in FIGS. 1 and 3, the footswitch 5 includes the two pedal switches 17a and 17b. The switch detection unit 22, therefore, includes two switch detection circuits 22a and 22b in accordance with the structure of the footswitch 5. The structure of switch detection circuit 22a will be described below (see FIG. 6).

Referring to FIG. 3, the relay device 6 further includes an ultrasonic output control unit 24 and a high-frequency output control unit 25. The ultrasonic output control unit 24 comprises a switch element 24a. The high-frequency output control unit 25 comprises a switch element 25a.

Referring to FIG. 2, the ultrasonic output control unit 24 is connected to a footswitch connector 27 for ultrasonic surgery device (abbreviated to ultrasonic connector) of the ultrasonic surgical device 3 through the ultrasonic surgical device connecting cable 20.

The high-frequency output control unit 25 is connected to a footswitch connector 28 for electrosurgical device (abbreviated to high-frequency connector) of the electrosurgical device 4 through the electrosurgical device connecting cable 21.

Referring to a specific example in FIG. 3, the switch elements 24a and 25a, respectively constituting the ultrasonic output control unit 24 and the high-frequency output control unit 25, each comprise a photocoupler. In each photocoupler, an output signal corresponding to an input signal is generated while electrical isolation between input and output is kept. More specifically, an input signal is output through photo-coupled means, thus providing electrical isolation between the ground (GND) on the input signal side and that on the output signal side, as will be described below.

When electric signals output from the control unit 23 are supplied to light emitting diodes (LEDs) 29a and 30a of the photocouplers, respectively constituting the switch elements 24a and 25a, the LEDs 29a and 30a emit light rays.

The light rays are received by phototransistors (or photodiodes) 29b and 30b which face the LEDs 29a and 30a, respectively. Thus, the phototransistors 29a and 30a are switched to a conduction mode, i.e., the ON state (switch-on) from the OFF state in which no light rays are received.

Binary signals indicative of the switch-on (or switch-off) states of the phototransistors 29b and 30b are transmitted to the ultrasonic surgical device 3 and the electrosurgical device 4 through the ultrasonic surgical device connecting cable 20 and electrosurgical device connecting cable 21, respectively.

In FIG. 3, the photocouplers are used as the switch elements 24a and 25a. *Relay switches may be used.*

Figure 4:
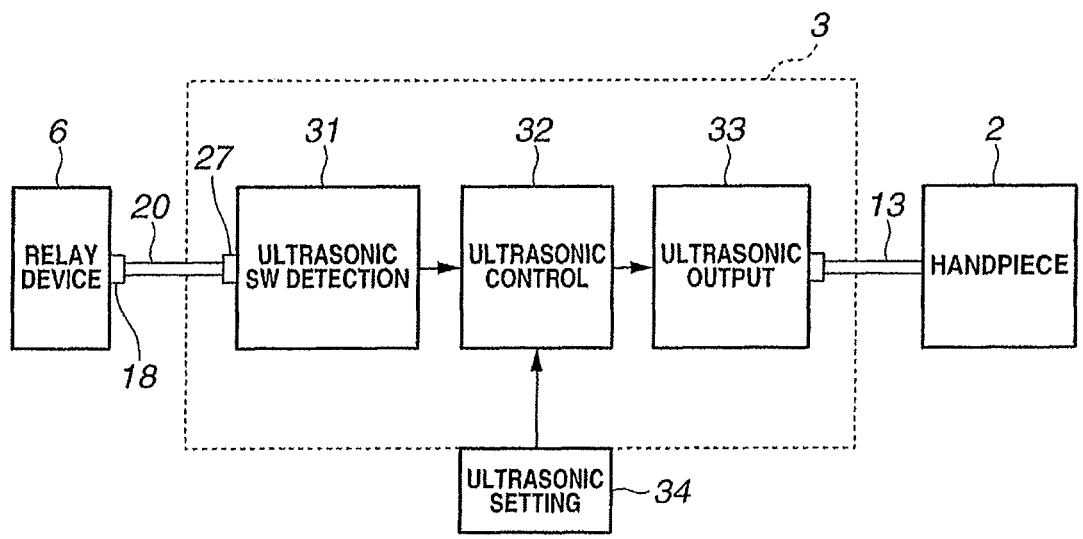
FIG. 4 is a block diagram illustrating the internal structure of an ultrasonic surgical device.

FIG. 4 shows the internal structure of the ultrasonic surgical device 3.

The ultrasonic surgical device 3 includes an ultrasonic switch (SW) detection unit 31 for detecting a switch-on/off signal (output or stop instruction), the signal being supplied through the footswitch connector 27 for ultrasonic surgery device.

A footswitch 94 (see FIG. 24) dedicated to the ultrasonic surgical device 3 can be detachably connected to the footswitch connector 27 for ultrasonic surgery device of the ultrasonic surgical device 3, as will be described later. The ultrasonic switch detection unit 31 also detects a switch-on/off signal indicative of the turn-on/off of the dedicated footswitch 94 for ultrasonic power supply.

In other words, the switch element 24a generates a signal having compatibility with a signal generated upon turning on/off the footswitch 94. Since the footswitch 94 has two pedal switches, the ultrasonic output control unit 24 may include two switch elements 24a.

Similarly, the switch element 25a generates a signal having compatibility with a signal generated upon turning on/off a footswitch 95 (see FIG. 24) dedicated to the electrosurgical device. Since the footswitch 95 has two pedal switches, the high-frequency output control unit 25 may include two switch elements 25a.

Referring to FIG. 4, when detecting a switch-on signal for ultrasonic power supply, the ultrasonic switch detection unit 31 outputs an ultrasonic switch-on signal to an ultrasonic control unit 32.

In accordance with the ultrasonic switch-on signal, the ultrasonic control unit 32 outputs an ultrasonic output signal to an ultrasonic output unit 33. In response to the ultrasonic output signal, the ultrasonic output unit 33 outputs an ultrasonic signal to the handpiece 2 connected via the ultrasonic handpiece cable 13.

The ultrasonic surgical device 3 includes an ultrasonic setting unit 34 which is disposed in, for example, a front panel. The operator manipulates a setup button of the ultrasonic setting unit 34 to change an output value of an ultrasonic signal output from the ultrasonic output unit 33 or select an ultrasonic output mode, such as a continuous output mode or an intermittent pulse output mode, through the ultrasonic control unit 32.

In other words, the ultrasonic-signal output mode can be changed by operating a setup button of the ultrasonic setting unit 34 and the like.

Figure 5:
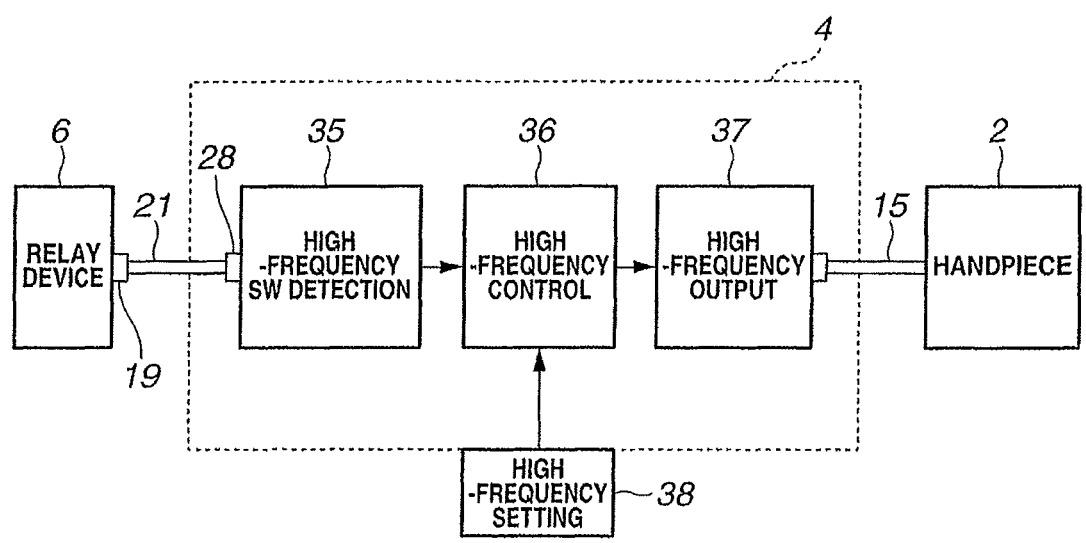
FIG. 5 is a block diagram illustrating the internal structure of an electrosurgical device.

FIG. 5 shows the internal structure of the electrosurgical device 4.

The electrosurgical device 4 includes a high-frequency switch detection unit 35 for detecting a switch-on/off signal (output or stop instruction), the signal being supplied through the connector 28.

The footswitch 94 (see FIG. 24) dedicated to the electrosurgical device 4 can be detachably connected to the connector 28 of the electrosurgical device 4, as will be described later. The high-frequency switch detection unit 35 also detects a switch-on/off signal indicative of the turn-on/off of the dedicated footswitch 95 for high-frequency power supply.

When detecting a switch-on signal for high-frequency power supply, the high-frequency switch detection unit 35 outputs a high-frequency switch-on signal to a high-frequency control unit 36.

In accordance with the high-frequency switch-on signal, the high-frequency control unit 36 outputs a high-frequency output signal to a high-frequency output unit 37. In response to the high-frequency output signal, the high-frequency output unit 37 outputs a high-frequency signal to the handpiece 2 connected via the high-frequency handpiece cable 15.

The electrosurgical device 4 includes a high-frequency setting unit 38 which is disposed in, for example, a front panel. The operator manipulates a setup button of the high-frequency setting unit 38 or the like to change an output value of an ultrasonic signal output from the high-frequency output unit 37 or select a high-frequency output mode, such as a continuous output mode or an intermittent pulse output mode, through the high-frequency control unit 36.

In other words, the high-frequency-signal output mode can be changed by operating a setup button of the high-frequency setting unit 38 or the like.

Figure 6:
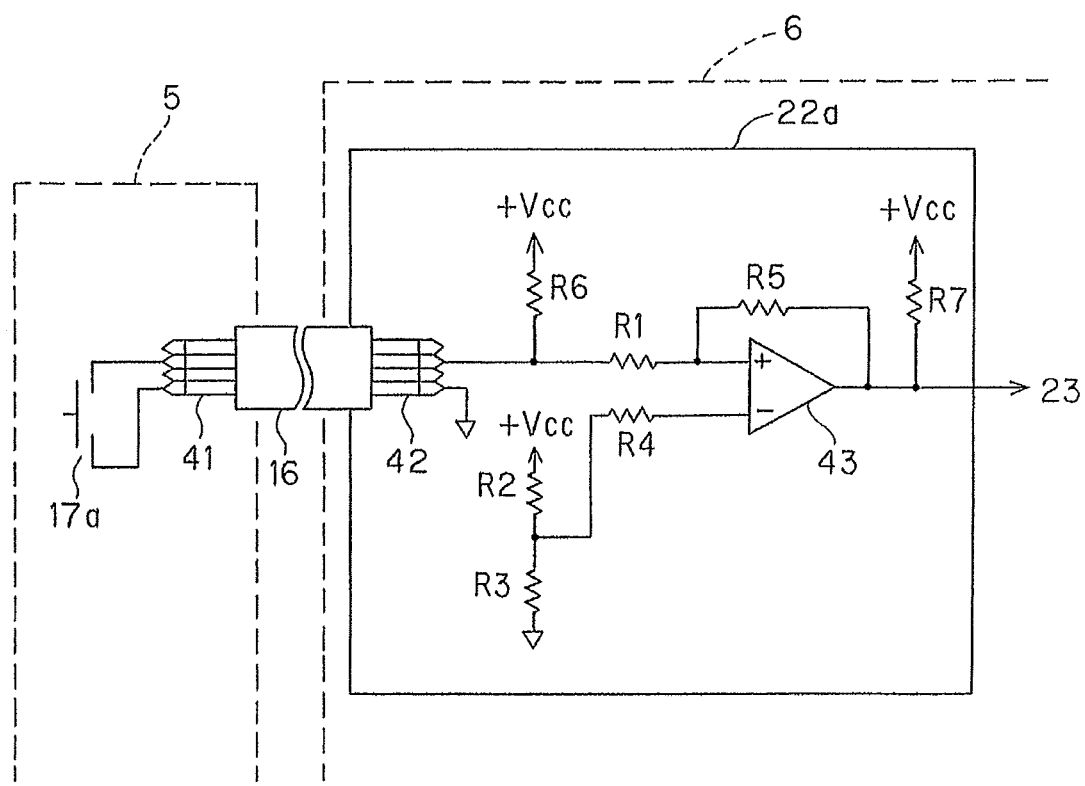
FIG. 6 is a circuit diagram showing the structure of a switch detection unit of the relay device.

FIG. 6 shows the structure of the switch detection circuit 22a, which constitutes the switch detection unit 22 which detects the operation of the footswitch 5 in the relay device 6.

When the footswitch 5 is connected to the relay device 6 through the cable 16, a connector 41 (connected to the pedal switch) of the footswitch 5 is electrically connected to a connector 42 connected to the switch detection circuit 22a of the relay device 6.

The connector 41 on the footswitch side is connected to the pedal switch 17a in the footswitch 5. The operator steps on the pedal switch 17a, thus changing the OFF state of a contact of the pedal switch 17a to the ON state. The operator stops stepping on the pedal switch 17a, thus changing the ON state of the pedal switch 17a to the OFF state.

A switch-on/off signal, serving as an operation signal indicative of the operation state of the pedal switch 17a, is supplied to a comparator 43 in the switch detection circuit 22a through the connector 42 on the relay device side.

The operation signal is supplied to a non-inverting input terminal of the comparator 43 through a resistor R1. A reference voltage, obtained by dividing a voltage (for example, 5V) at a power supply terminal Vcc through resistors R2 and R3, is applied to an inverting input terminal of the comparator 43 via a resistor R4.

The non-inverting input terminal of the comparator 43 is connected to an output terminal thereof through a resistor R5. One terminal of the connector 42 on the relay device side, to which the operation signal is supplied, is connected to the power supply terminal Vcc through a pull-up resistor R6. The other terminal of the connector 42 is grounded.

The output terminal of the comparator 43 is connected to the power supply terminal Vcc through a pull-up resistor R7. The output terminal of the comparator 43 serves as an output terminal of the switch detection unit 22. An output signal of the comparator 43 is supplied to the control unit 23.

The footswitch 5 has the two pedal switches 17a and 17b as shown in FIGS. 1 and 3. As will be described below, in an individual control mode, the pedal switch 17a can be used to turn on and off the ultrasonic surgical device 3 and the other pedal switch 17b can be used to turn on and off the electrosurgical device 4.

In a simultaneous control mode, the pedal switch 17a can be used to turn on and off both the ultrasonic surgical device 3 and the electrosurgical device 4.

The relay device 6 has the switch detection unit 22 including the switch detection circuits 22a and 22b which correspond to the two pedal switches 17a and 17b, respectively. The switch detection circuit 22b has the same structure as that of the switch detection circuit 22a shown in FIG. 6.

In the switch detection unit 22 with the above structure, when the pedal switch 17a is in the OFF state, a voltage level at the non-inverting input terminal of the comparator 43 is equal to a voltage Vcc at the power supply terminal Vcc (for brevity, voltage of the power supply terminal is also shown as Vcc). The voltage Vcc is higher than the reference voltage at the inverting input terminal. Accordingly, an output of the comparator 43 is to a level "H" (high).

When the pedal switch 17a is changed from the OFF state to the ON state, the voltage level at the non-inverting input terminal becomes 0V (i.e., ground level), which is lower than the reference voltage. An output of the comparator 43, therefore, goes to a level "L" (low).

As described above, the output level of the comparator 43 reflects the ON or OFF state of the pedal switch 17a. The control unit 23 receives the output signal of the comparator 43 and controls the output modes and output timings of the devices 3 and 4 in accordance with the received signal.

When the pedal switches 17a and 17b of the footswitch 5 are operated, the control unit 23 outputs electric signals, which correspond to the operation states of the pedal switch 17a and 17b of the footswitch 5, to the ultrasonic output control unit 24 and the high-frequency output control unit 25 in accordance with the output modes and output timings preset through the ultrasonic surgical device 3 and the electrosurgical device 4.

Figure 7:
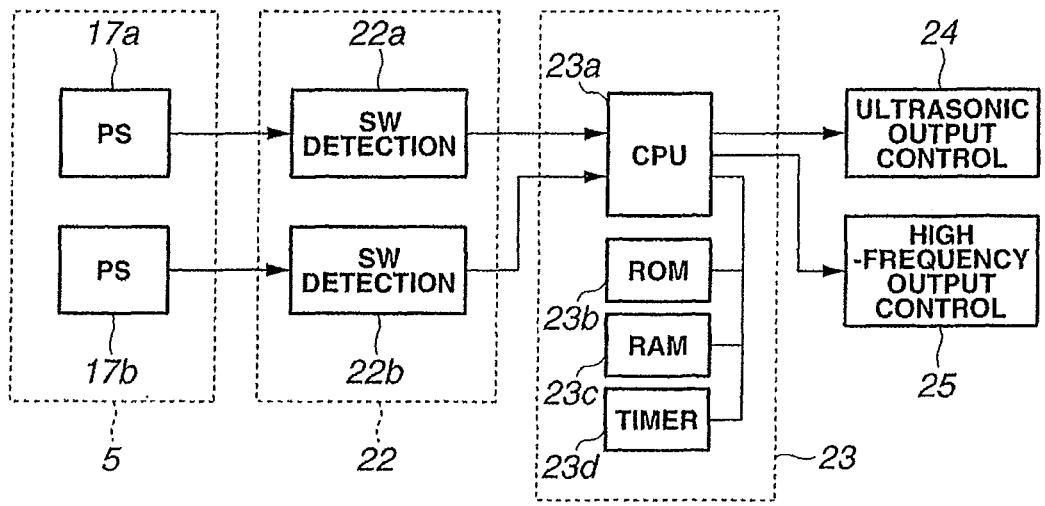
FIG. 7 is a block diagram showing the structure of a control unit of the relay device.

Referring to FIG. 7, the control unit 23 includes a CPU 23a, an ROM 23b, an RAM 23c, and a timer 23d. The CPU 23a performs the control operation. The ROM 23b stores a control program. The RAM 23c is used as a work area and is also used for temporal data storage. The timer 23d is used for timing control through the CPU 23a. The CPU 23a changes the output modes and output timings in accordance with the program stored in the ROM 23b. In other words, the CPU 23a has a function for controlling the output modes and output timings of the devices 3 and 4.

In the description of the present embodiment, it is assumed that the output timings cannot be changed during the operation of the system and only the preset output timings are used (the structure and operation in which output timings can be changed during the operation will be described in a second embodiment). In the present embodiment, an output mode is set in each of the ultrasonic surgical device 3 and the electrosurgical device 4.

In accordance with a pedal-switch change signal, the CPU 23a switches an output control mode between the simultaneous control mode and the individual control mode. In the simultaneous control mode, a common switch-on signal is output to each of the ultrasonic surgical device 3 and the electrosurgical device 4 in accordance with the ON/OFF operation of the pedal switch 17a. In the individual control mode, switch-on/off signals of the pedal switches 17a and 17b are output to the ultrasonic surgical device 3 and the electrosurgical device 4, respectively.

Specifically, the CPU 23a recognizes an input of a pedal-switch change signal when both the pedal switches 17a and 17b are in the ON state for a predetermined period of time or longer within a short period of time after, for example, power-on. The CPU 23a then switches the output control mode to another one.

After that, when both of the pedal switches 17a and 17b are turned off, the switch detection unit 22 of the relay device 6 performs the operation based on the ON/OFF operation of the footswitch 5 in the set output control mode.

Changing the output control mode is not limited to the above-described way. A pedal-switch selector switch (not shown) may be connected to the CPU 23a and the output control mode may be changed using this switch.

Figure 8A:
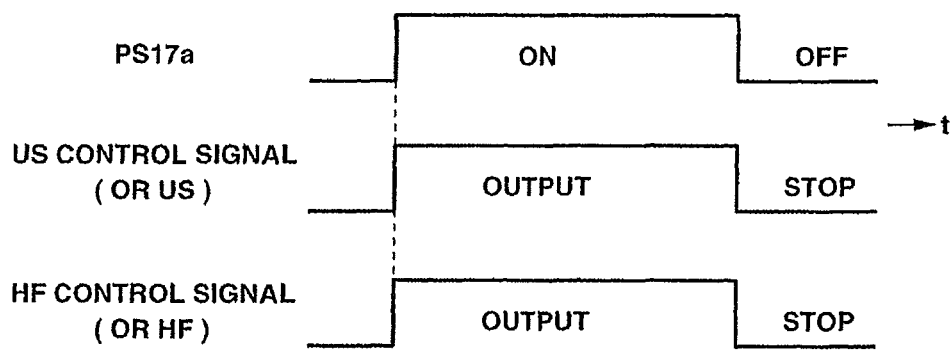
FIG. 8A is a timing diagram of the operation in which ultrasonic and high-frequency outputs are simultaneously controlled in accordance with a manipulation of one pedal switch included in a footswitch.
Figure 8B:
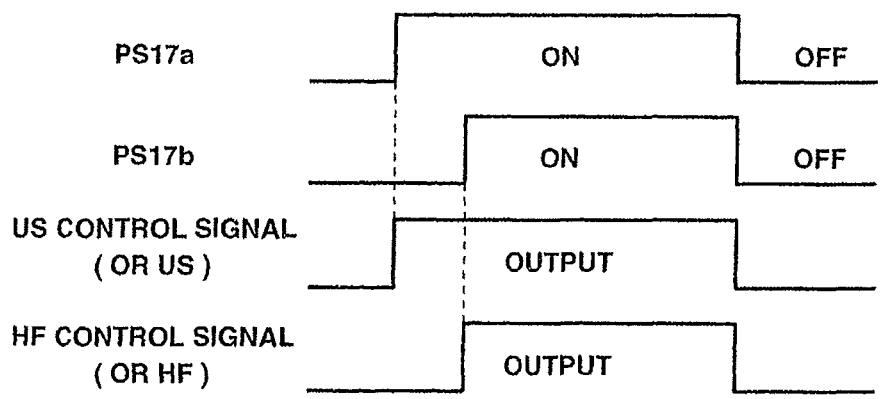
FIG. 8B is a timing diagram of the operation in which ultrasonic and high-frequency outputs are individually controlled in accordance with manipulations of pedal switches in the footswitch.

When the output control mode in which common switch-ON signal is output to both the ultrasonic surgical device 3 and electrosurgical device 4 in response to ON/OFF operation of the one pedal switch 17a of the two pedal switches is set to the simultaneous control mode in response to the pedal-change switch signal, as shown in FIG. 8A, an ultrasonic control signal and a high-frequency control signal are simultaneously output in accordance with the operation of the pedal switch 17a as shown in FIG. 8A. In FIGS. 8A and 8B, the lateral direction represents time t.

On the other hand, when the output control mode is set to the individual control mode in response to the pedal-change switch, an ultrasonic control signal and a high-frequency control signal are individually output by operating the respective pedal switches 17a and 17b as shown in FIG. 8B.

According to the present embodiment, as described above, the single footswitch 5 is connected to the relay device 6 so that the operations of the ultrasonic surgical device 3 and the electrosurgical device 4 can be controlled by operating the footswitch 5.

The ultrasonic switch detection unit 31 of the ultrasonic surgical device 3 and the high-frequency switch detection unit 35 of the electrosurgical device 4 can have the same structure as that of the switch detection circuit 22a of the relay device 6 shown in FIG. 6.

Figure 24:
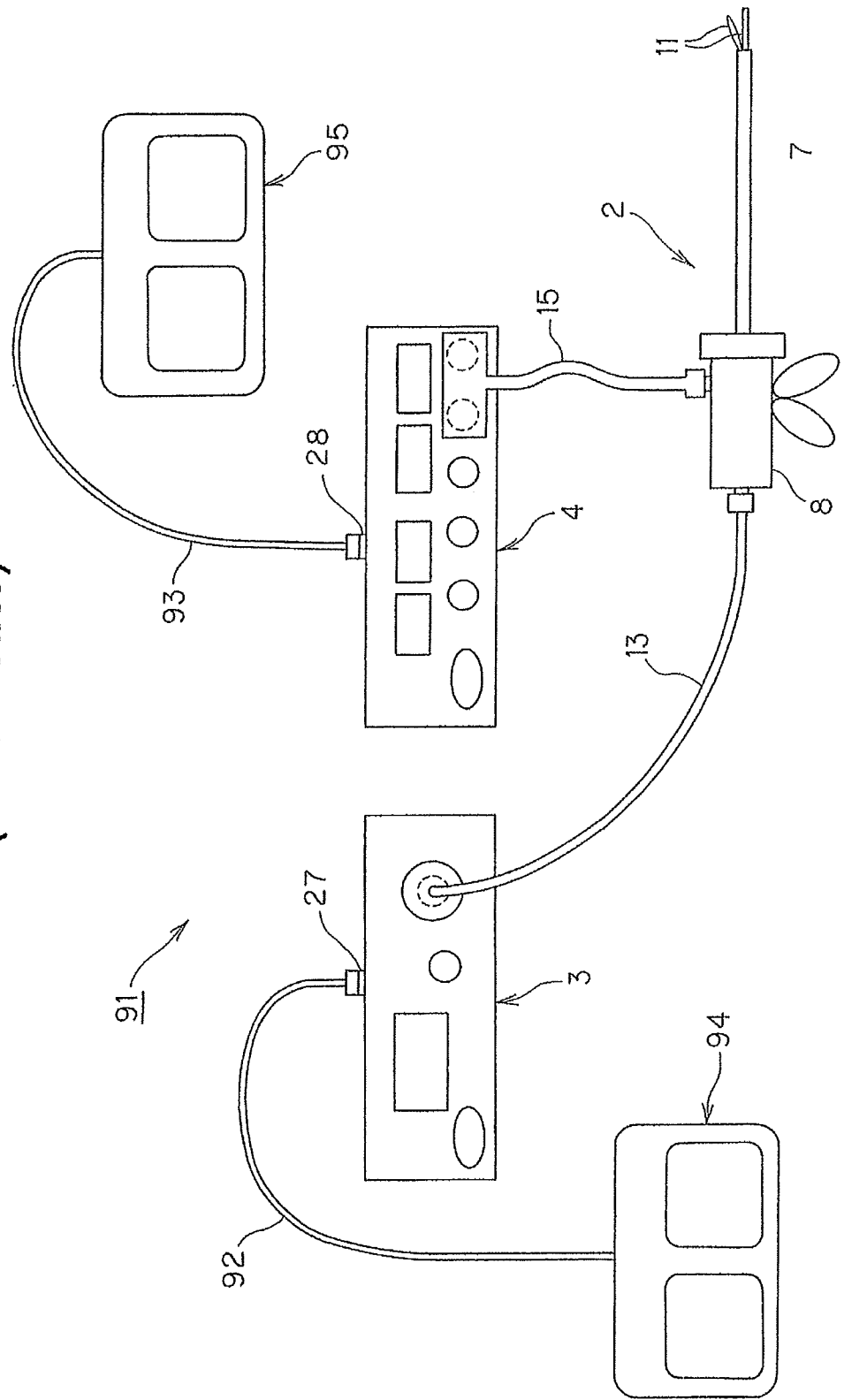
FIG. 24 is an external view of a conventional ultrasonic-surgical and electrosurgical system.

The ultrasonic-surgical and electrosurgical system 1 having the relay device 6, shown in FIGS. 1 and 2, according to the present embodiment is obtained by improving a conventional ultrasonic-surgical and electrosurgical system 91 shown in FIG. 24.

The conventional ultrasonic-surgical and electrosurgical system 91 includes a handpiece 2, an ultrasonic surgical device 3, an electrosurgical device 4, the footswitch 94 connected to the ultrasonic surgical device 3 via a footswitch cable 92, and the footswitch 95 connected to the electrosurgical device 4 via a footswitch cable 93.

In the conventional system, the handpiece 2, the ultrasonic surgical device 3, and the electrosurgical device 4 have the same structures as those described with reference to FIG. 1.

In the ultrasonic-surgical and electrosurgical system 91 with the structure shown in FIG. 24, the ultrasonic surgical device 3 and the electrosurgical device 4 are controlled in accordance with the ON/OFF operations of the footswitches 94 and 95, respectively.

In this conventional system, an ultrasonic switch detection unit 31 (see FIG. 4) of the ultrasonic surgical device 3 detects the turn-on/off of the footswitch 94. When detecting the turn-on, the ultrasonic switch detection unit 31 outputs an ultrasonic switch-on signal to an ultrasonic control unit 32 in a manner similar to the present embodiment.

Similarly, a high-frequency switch detection unit 35 (see FIG. 5) of the electrosurgical device 4 detects the turn-on/off of the footswitch 95. When detecting the turn-on, the high-frequency switch detection unit 35 outputs a high-frequency switch-on signal to a high-frequency control unit 36 as described above.

According to the present embodiment, the ultrasonic-surgical and electrosurgical system 1 includes the relay device 6 and the single footswitch 5 in place of the two footswitches 94 and 95 shown in FIG. 1.

The footswitch 5 may be the footswitch 94 dedicated to the ultrasonic surgical device, the footswitch 95 dedicated to the ultrasonic surgical device, or a footswitch dedicated to the relay device 6. Alternatively, a hand switch may be used instead of the footswitch 5. The operator holds the hand switch and turns on and off the switch with the holding hand.

The operation of the ultrasonic-surgical and electrosurgical system 1 with the above-described structure according to the present embodiment will now be described with reference to FIGS. 1, 2, and 9.

To perform a treatment using ultrasonic vibration and high-frequency current, the operator arranges and connects the components of the ultrasonic-surgical and electrosurgical system 1 as shown in FIGS. 1 and 2.

In this case, the operator connects the ultrasonic surgical device 3 to the relay device 6 using the ultrasonic surgical device connecting cable 20 and connects the electrosurgical device 4 to the relay device 6 using the electrosurgical device connecting cable 21. The cables 20 and 21 are connectable to the corresponding connectors 27 and 28 provided for the ultrasonic surgical device 3 and the electrosurgical device 4, respectively.

The operator connects the footswitch 5 to the relay device 6 via the footswitch cable 16. In addition, the operator connects the handpiece 2 to the ultrasonic surgical device 3 and the electrosurgical device 4 via the cables 13 and 15, respectively.

Then, the operator turns on respective power switches in the ultrasonic-surgical and electrosurgical system 1. In addition, the operator initializes the ultrasonic surgical device 3, the electrosurgical device 4, and the relay device 6. As for initialization, the operator sets a power level of the ultrasonic surgical device 3 and a power mode of the electrosurgical device 4, such as a coagulation mode or an incision mode. The operator also sets the output control mode, such as the simultaneous control mode or the individual control mode, in the relay device 6 using a pedal-switch change signal.

Figure 9:
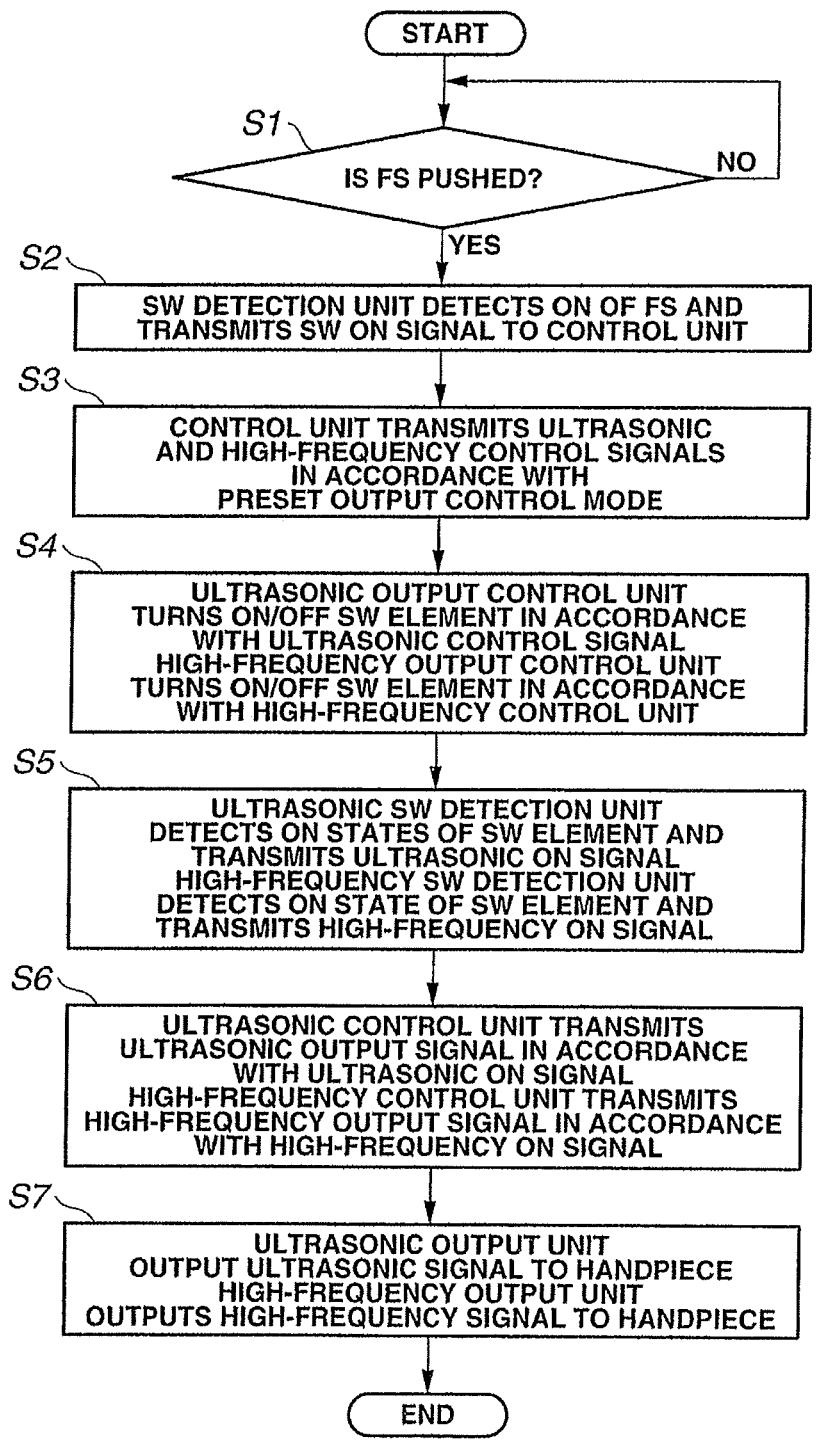
FIG. 9 is a flowchart of the operation of the ultrasonic-surgical and electrosurgical system according to the first embodiment.

Referring to FIG. 9, the switch detection unit 22 of the relay device 6 enters a standby mode in step S1. In the standby mode, the switch detection unit 22 waits for the operation of pushing the footswitch (abbreviated to FS in FIG. 9) 5.

More specifically, in the simultaneous control mode, the operation of pushing the pedal switch 17a (or 17b) is detected. In the individual control mode, the operation of pushing the pedal switch 17a and that of pushing the pedal switch 17b are detected. In the following description, for the sake of simplicity, it is assumed that the simultaneous control mode is set.

When the operator pushes the footswitch 5, the switch detection unit 22 detects the pushed state of the footswitch 5 and outputs a switch-on signal to the control unit 23, as shown in step S2.

As shown in step S3, when receiving the switch-on signal, the control unit 23 outputs an ultrasonic control signal and a high-frequency control signal to the ultrasonic output control unit 24 and the high-frequency output control unit 25 in accordance with the preset output control mode, respectively.

In this instance, the output control mode includes parameters, e.g., an ultrasonic power level, ultrasonic-output start time, ultrasonic-output stop time, the high-frequency power mode, such as the coagulation mode or the incision mode, high-frequency-output start time, and high-frequency-output stop time.

When receiving the ultrasonic control signal, the ultrasonic output control unit 24 turns on/off the switch element 24a in accordance with the received signal in step S4.

When receiving the high-frequency control signal, the high-frequency output control unit 25 turns on/off the switch element 25a in accordance with the received signal in step S4.

The ultrasonic output control unit 24 is connected to the ultrasonic switch detection unit 31 of the ultrasonic surgical device 3 via the ultrasonic surgical device connecting cable 20.

Thus, as shown in step S5, the ultrasonic switch detection unit 31, therefore, detects the turn-on/off of the switch element 24a as in the case of the turn-on/off of the dedicated footswitch 94.

The ultrasonic switch detection unit 31 transmits a detected ultrasonic switch-on/off signal to the ultrasonic control unit 32.

The high-frequency output control unit 25 is connected to the high-frequency switch detection unit 35 of the electrosurgical device 4 via the electrosurgical device connecting cable 21.

Accordingly, the high-frequency switch detection unit 35 detects the turn-on/off of the switch element 25a as in the case of the turn-on/off of the dedicated footswitch 95.

The high-frequency switch detection unit 35 transmits a high-frequency switch-on/off signal to the high-frequency control unit 36.

In step S6, the ultrasonic control unit 32 transmits an ultrasonic output/output-stop signal to the ultrasonic output unit 33 in accordance with the ultrasonic switch-on/off signal. Similarly, the high-frequency control unit 36 transmits a high-frequency output/output-stop signal to the high-frequency output unit 37 in accordance with the high-frequency switch-on/off signal when receiving a high-frequency switch-off signal.

In step S7, the ultrasonic output unit 33 outputs an ultrasonic driving signal corresponding to the ultrasonic output/output-stop signal to the handpiece 2 via the handpiece cable 13.

The high-frequency output unit 37 outputs a high-frequency signal corresponding to the high-frequency output/output-stop signal to the handpiece 2 via the high-frequency handpiece cable 15.

In the above-described operation, the operator can perform a treatment on the biological tissue 45 using ultrasonic vibrations and high-frequency current by turning on and off operation of the footswitch 5 while holding the handpiece 2.

In the simultaneous control mode, ultrasonic power and high-frequency power can be simultaneously controlled by operating the pedal switch 17a serving as one switch element, as shown in, for example, FIG. 8A.

In the individual control mode, ultrasonic power and high-frequency power can be individually controlled. In this case, ultrasonic power and high-frequency power can be controlled using only the footswitch 5, thus improving the operability.

In the system disclosed in Japanese Unexamined Patent Application Publication No. 2003-33369, an ultrasonic surgical device and an electrosurgical device simultaneously output ultrasonic vibration and high-frequency current, leading to a restricted range of medical treatments using this system. In contrast, with the present embodiment, ultrasonic vibration and high-frequency current can be controlled individually as described above.

The present embodiment has the following advantages: In the ultrasonic-surgical and electrosurgical system 1, the operator can control outputs of both of the ultrasonic surgical device 3 and the electrosurgical device 4 by operating only the footswitch 5 connected to the relay device 6.

In other words, the operator can control outputs of both the devices 3 and 4 using the single common footswitch 5 instead of the two footswitches 94 and 95 in the conventional system 91, resulting in improvement of the operability.

Advantageously, the operator can easily manipulate the switch during a treatment.

In addition, since the number of footswitches is reduced, an operating room becomes clear. Specifically, the number of cables arranged around the operator's feet can be reduced.

In the ultrasonic-surgical and electrosurgical system 1 according to the present embodiment, a switch-on/off signal is supplied from the relay device 6 to each of the ultrasonic surgical device 3 and the electrosurgical device 4. The switch-on/off signal has compatibility with those generated when the existing footswitches are directly operated.

In the use of the relay device 6, therefore, the existing ultrasonic surgical device 3 connectable to the dedicated footswitch 94 and the existing electrosurgical device 4 connectable to the dedicated footswitch 95 shown in FIG. 24 can be used as the devices ultrasonic surgical 3 and electrosurgical 4 in the present system.

In other words, in the use of the relay device 6, an ultrasonic surgical device and an electrosurgical device dedicated to the relay device 6 are not required. The existing ultrasonic surgical device 3 and electrosurgical device 4 can be used.

In the present embodiment, signal transmission and reception between the relay device 6 and each of the ultrasonic surgical device 3 and the electrosurgical device 4 are performed using the photocouplers. Accordingly, ground isolation between the devices can be provided, so that the devices can be kept electrically isolated from each other.

Second Embodiment

A second embodiment of the present invention will now be described with reference to FIGS. 10 to 14C. The fundamental structure of an ultrasonic-surgical and electrosurgical system according to the second embodiment is the same as that according to the first embodiment. The ultrasonic-surgical and electrosurgical system according to the present embodiment includes a relay device 6B partially different from the relay device 6 of the system 1 in FIGS. 1 and 2.

As will be described below, the relay device 6B according to the present embodiment further has parameter setting means that is not included in the relay device 6 according to the first embodiment. The parameter setting means readily changes an output control mode and an output timing pattern.

A user, e.g., an operator, changes settings on the parameter setting means so that an ultrasonic surgical device 3 and an electrosurgical device 4 can be operated in output modes and output timing patterns.

Figure 10:
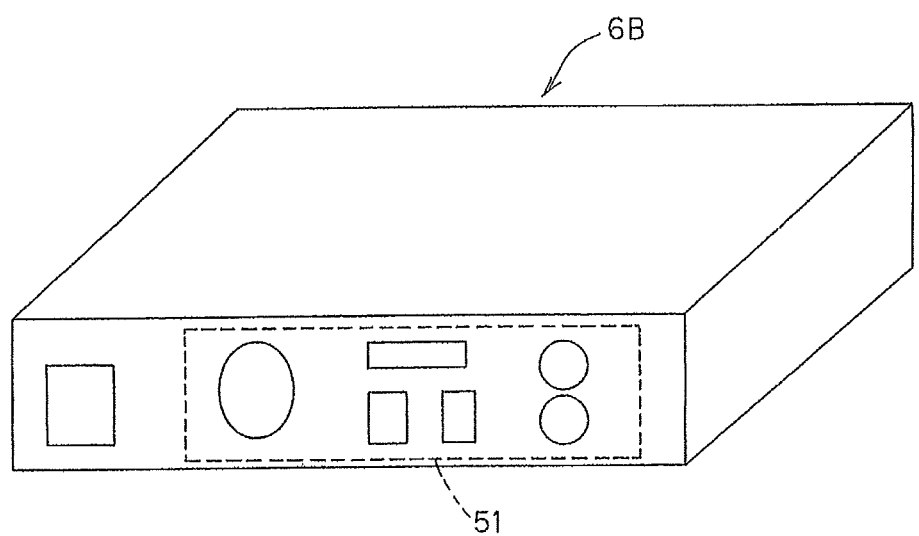
FIG. 10 is an external view of a relay device according to a second embodiment of the present invention.

FIG. 10 shows the external view of the relay device 6B of the present embodiment. The relay device 6B according to the present embodiment has a parameter switch 51 in the front face thereof. The parameter switch 51 is used for setting of an output control mode (including parameters, i.e., an ultrasonic power level, ultrasonic-output start time, ultrasonic-output stop time, a high-frequency power mode (coagulation or incision), high-frequency-output start time, and high-frequency-output stop time).

The parameter switch 51 includes a plurality of switch elements. The ultrasonic-surgical and electrosurgical system including the relay device 6B according to the present embodiment can be operated in a plurality of output mode patterns by combining settings of those switch elements.

Figure 11:
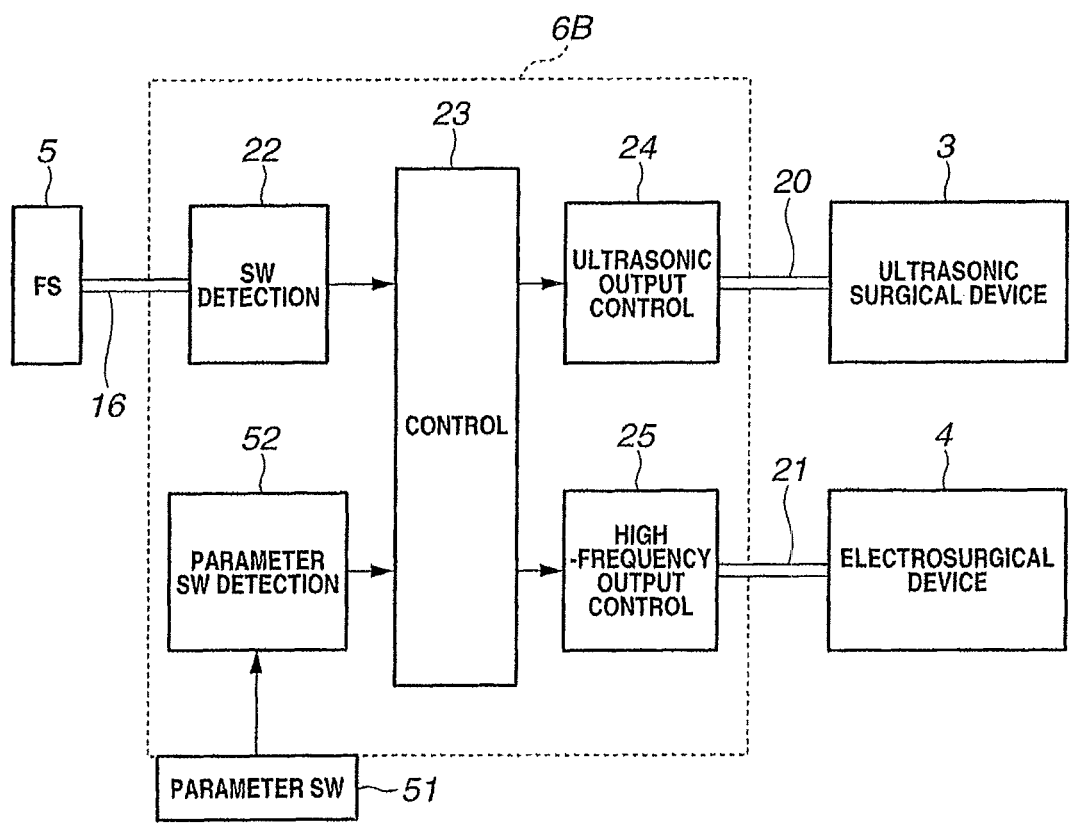
FIG. 11 is a block diagram illustrating the internal structure of the relay device.

FIG. 11 shows the structure of the relay device 6B according to the present embodiment. As compared to the relay device 6 in FIG. 2, the relay device 6B further includes the parameter switch 51 and a parameter-switch detection unit 52 for detecting the state of the parameter switch 51.

Figure 12:
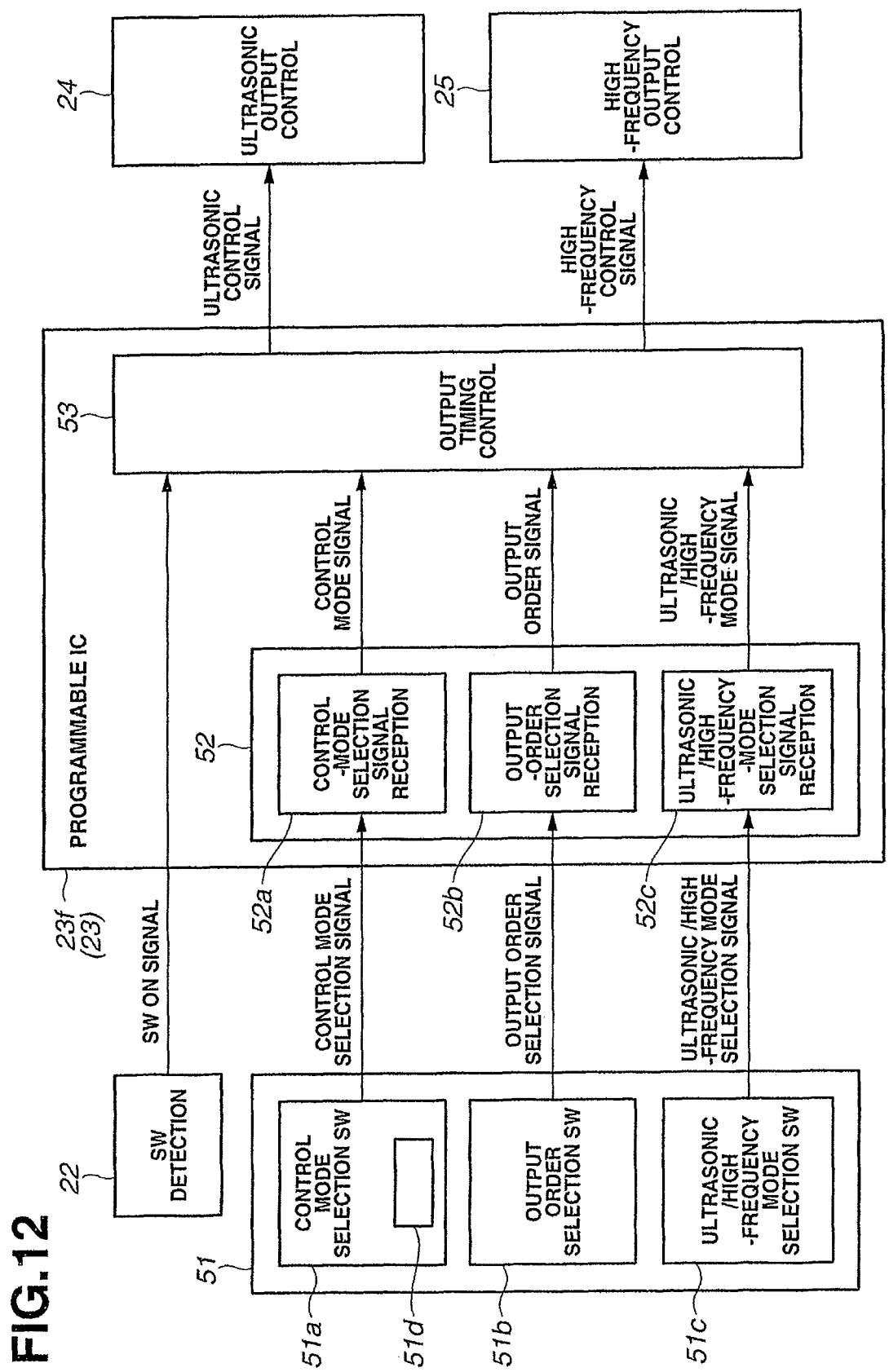
FIG. 12 is a block diagram showing functional blocks in the control unit including a programmable IC and those in the vicinity of the control unit.

A control unit 23 constitutes the relay device 6B. In the first embodiment, the control unit 23 includes the CPU 23a and the like. In the second embodiment, the control unit 23 may include a programmable IC 23f as shown in FIG. 12. The programmable IC 23f is a device including a plurality of small programmable logic elements integrated.

In the present embodiment, a functional logic is designed using the programmable IC 23f as shown in FIG. 12. Referring to FIG. 12, the programmable IC 23f includes a function of the control unit 23 and that of the parameter-switch detection unit 52 in FIG. 11. The programmable IC 23f may include only the control unit 23.

Referring to FIG. 12, the parameter switch 51 includes a control mode selection switch 51a, an output order selection switch 51b, and an ultrasonic/high-frequency mode selection switch 51c. The control mode selection switch 51a is used for selection between a continuous output mode, an intermittent output mode, and a type-specific control mode suitable for the type of a handpiece 2. The type-specific control mode will be described later. The output order selection switch 51b is used for selection of the order of ultrasonic output and high-frequency output. The ultrasonic/high-frequency mode selection switch 51c is used for selection between an ultrasonic mode and a high-frequency mode.

In addition to the selection of the order of ultrasonic output and high-frequency output, output timings (for example, times Ta and Tb in FIG. 14A, which will be described below) can be set in the selected order using the output order selection switch 51b.

The respective selection switches 51a to 51c output selection signals. The parameter-switch detection unit 52 includes a control mode selection signal reception section 52a, an output order selection signal reception section 52b, and an ultrasonic mode/a high-frequency mode selection signal reception section 52c. The control mode selection signal reception section 52a detects the selection signal output from the control mode selection switch 51a. The output order selection signal reception section 52b detects the selection signal output from the output order selection switch 51b. The ultrasonic mode/the high-frequency mode selection signal reception section 52c detects the selection signal output from the ultrasonic/high-frequency mode selection switch 51c.

The control mode selection signal reception section 52a outputs a control mode signal to an output timing control unit 53. The output order selection signal reception section 52b outputs an output order signal to the timing control unit 53. The ultrasonic mode/the high-frequency mode selection signal reception section 52c outputs an ultrasonic/high-frequency mode signal to the timing control unit 53.

In addition, a switch detection unit 22 outputs a switch-on signal to the output timing control unit 53.

In accordance with selected parameters on the parameter switch 51, the output timing control unit 53 outputs an ultrasonic control signal and a high-frequency control signal to an ultrasonic output control unit 24 and a high-frequency output control unit 25, respectively. In the present embodiment, the ultrasonic control signal and the high-frequency control signal are used for changing of output timings and output modes, as typically shown in FIGS. 14A to 14C which will be described later.

The control mode selection switch Ma, constituting the parameter switch 51, also has a function of a pedal-switch change switch 51d for generating a pedal-switch change signal, which has been described in the first embodiment. As described in the first embodiment, one of the simultaneous control mode and the individual control mode can be selected.

In the first embodiment, the output control mode cannot be switched to the other mode using the relay device 6 during the operation of the system. According to the present embodiment, the operator can readily change the output control mode by manipulating the pedal-switch change switch 51d in the relay device 6B during the operation of the system. In addition, output timings or the like can be easily changed through the parameter switch 51.

The other components of the system according to the present embodiment are the same as those described in the first embodiment. The previously described components, therefore, are designated by the same reference numerals.

As described above, the relay device 6B according to the present embodiment includes the switch detection unit 22, the control unit 23, the ultrasonic output control unit 24, the high-frequency output control unit 25, the parameter switch 51, and the parameter-switch detection unit 52.

A footswitch 5 is connected to the switch detection unit 22 via a footswitch cable 16 in a manner similar to the first embodiment. The ultrasonic output control unit 24 and the high-frequency output control unit 25 are connected to the ultrasonic surgical device 3 (i.e., an ultrasonic switch detection unit 31 included therein) and the electrosurgical device 4 (i.e., a high-frequency switch detection unit 35 included therein) via ultrasonic surgical device connecting cable 20 and electrosurgical device connecting cable 21, respectively.

The other structure and arrangement of the system according to the present embodiment are the same as those according to the first embodiment. The operation of the system according to the second embodiment will now be described.

When the footswitch 5 is pushed, the switch detection unit 22 detects the pushed state of the footswitch 5 and then transmits a switch-on signal to the control unit 23. The parameter-switch detection unit 52 transmits parameter switch signals to the control unit 23. The parameter switch signals are related to an output control mode set through the parameter switch 51.

When receiving the switch-on signal, the control unit 23 respectively outputs an ultrasonic control signal and a high-frequency control signal to the ultrasonic output control unit 24 and the high-frequency output control unit 25 in accordance with the parameter switch signals, i.e., in output modes at output timings set through the parameter switch 51.

The ultrasonic output control unit 24 turns on/off a switch element 24a in accordance with the received ultrasonic control signal.

The ultrasonic output control unit 24 is connected to the ultrasonic switch detection unit 31 of the ultrasonic surgical device 3 via the ultrasonic surgical device connecting cable 20. The ultrasonic switch detection unit 31, therefore, detects the turn-on/off of the switch element 24a as in the case of the turn-on/off of a footswitch 94 dedicated to the ultrasonic surgical device. The ultrasonic surgical device 3 outputs an ultrasonic signal to a handpiece 2 via an ultrasonic handpiece cable 13.

The high-frequency output control unit 25 turns on/off a switch element 25a in accordance with the received high-frequency control signal. The high-frequency output control unit 25 is connected to the high-frequency switch detection unit 35 of the electrosurgical device 4 via the electrosurgical device connecting cable 21. The high-frequency switch detection unit 35, therefore, detects the turn-on/off of the switch element 25a as in the case of the turn-on/off of a footswitch 95 dedicated to the electrosurgical device. The electrosurgical device 4 outputs a high-frequency signal to the handpiece 2 via a handpiece cable 15 for high-frequency current supply.

FIG. 13 is a flowchart of a series of operation steps according to the present embodiment. Since the flowchart of FIG. 13 is similar to that shown in FIG. 9, steps of FIG. 9 can also be used in FIG. 13.

In step S11, the operator manipulates the parameter switch 51 to set an output control mode.

In step S1, the switch detection unit 22 of the relay device 6B waits for the operation of pushing the footswitch 5 in the same way as the flowchart of FIG. 9. When the footswitch 5 is pushed, the switch detection unit 22 detects the turn-on of the footswitch 5 and transmits a switch-on signal to the control unit 23 in step S2.

According to the present embodiment, the parameter-switch detection unit 52 detects the parameters, representing the output control mode, set through the parameter switch 51. The parameter-switch detection unit 52 then transmits parameter switch signals to the control unit 23.

In step S13, the control unit 23 transmits an ultrasonic control signal and a high-frequency control signal to the ultrasonic output control unit 24 and the high-frequency output control unit 25 in accordance with the parameter switch signals, respectively.

Steps S4 to S7 following step S13 are the same as those in FIG. 7. A description of those steps is omitted.

The present embodiment has the same advantages as those of the first embodiment. In addition, a treatment can be performed in various output modes and output timings by changing parameters set through the parameter switch 51.

Figure 14A:
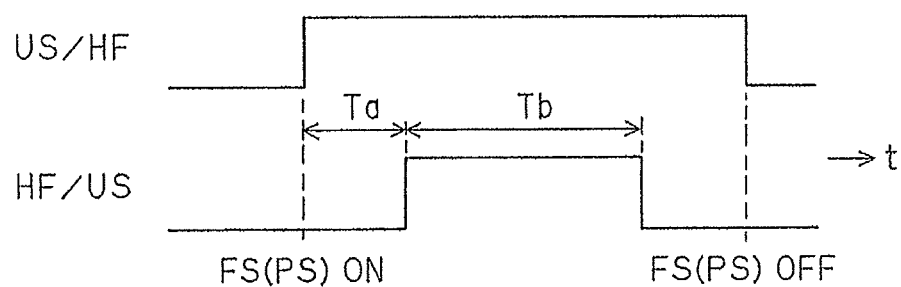
FIGS. 14A to 14C are timing diagrams of the operations in various output control modes in which both of ultrasonic and high-frequency outputs are controlled in accordance with a manipulation of a footswitch.
Figure 14B:
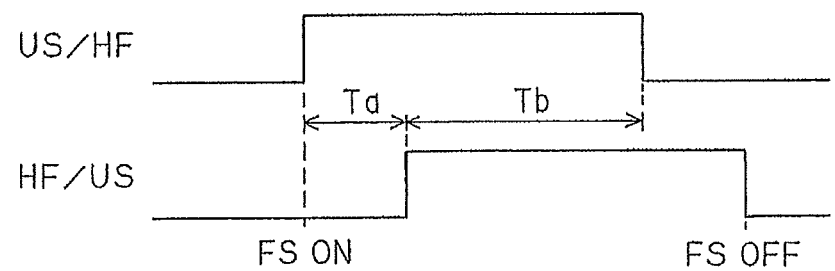
Figure 14C:
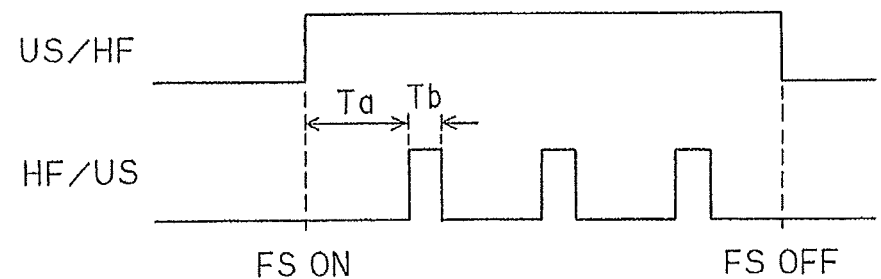

Parameters set through the parameter switch 51 are changed, so that various output (control) modes and output timing patterns can be set as shown in FIGS. 14A to 14C in addition to the modes and patterns in FIGS. 8A and 8B. FIGS. 14A to 14C show examples of the output control modes and the like set by operating, for example, one pedal switch 17a of the footswitch 5.

In the output control mode of FIG. 14A, when the footswitch 5 (i.e., the pedal switch 17a) is turned on, an ultrasonic control signal and an ultrasonic signal (which are abbreviated to US in the diagram) are output. After a lapse of time Ta after the turn-on of the footswitch 5, a high-frequency control signal and a high-frequency signal (which are abbreviated to "HF" in the diagram) are output for a period of time Tb. When the footswitch 5 is turned off, the output of the ultrasonic control signal and the ultrasonic signal is stopped.

The output control mode can be realized by settings selected through the output order selection switch 51b shown in FIG. 12.

In addition, another output control mode in which ultrasonic and high-frequency output patterns are interchanged can be set. Referring to FIG. 14A, therefore, the output control modes with different output patterns are represented using "US/HF" and "HF/US".

In the output control mode of FIG. 14B, when the footswitch 5 is turned on, an ultrasonic control signal and an ultrasonic signal are output for a period of time (Ta+Tb). After a lapse of time Ta after the turn-on of the footswitch 5, a high-frequency control signal and a high-frequency signal are output until the footswitch 5 is turned off.

In this case, another output control mode in which ultrasonic and high-frequency output patterns are interchanged can be set. Referring to FIG. 14B, therefore, the output control modes with different output patterns are represented using "US/HF" and "HF/US".

In the output control mode shown in FIG. 14C, when the footswitch 5 is turned on, an ultrasonic control signal and an ultrasonic signal are output. The ultrasonic output is continued until the footswitch 5 is turned off. On the other hand, after a lapse of time Ta after the turn-on of the footswitch 5, a high-frequency control signal and a high-frequency signal are output for a width of time Tb intermittently, i.e., each period (Ta+Tb).

In the use of intermittent output, an output value of the high-frequency signal can be selected in accordance with the type of the handpiece 2. In addition, the output waveform can be changed in accordance with a treatment mode (e.g., the incision mode or the coagulation mode).

In this case, another output control mode in which ultrasonic and high-frequency output patterns are interchanged can be set. Referring to FIG. 14C, therefore, the output control modes with different output patterns are shown using "US/HF" and "HF/US".

According to the present embodiment, the output and output-stop of ultrasonic and high-frequency energies can be controlled in various output modes and at different output timings.

The present embodiment has the following advantages:

Outputs of both the ultrasonic surgical device 3 and the electrosurgical device 4 can be controlled by operating the single footswitch 5 (or single pedal switch) connected to the relay device 6B. This arrangement enables the operator to readily manipulate switches during a treatment. In addition, since the number of switches is reduced, an operating room becomes clear.

In the present embodiment, signal transmission and reception between the relay device 6B and each of the ultrasonic surgical device 3 and the electrosurgical device 4 are performed using photocouplers. Accordingly, ground isolation between the devices can be provided, so that the devices can be kept electrically isolated from each other.

In addition, since the relay device 6B includes the parameter switch 51, a plurality of output modes and output timings for ultrasonic vibration and high-frequency current can be realized using various combinations of parameters set through the parameter switch 51. Thus, the setting and changing operations on the ultrasonic surgical device 3 and the electrosurgical device 4 can be minimized Advantageously, the operability can be improved.

In the ultrasonic-surgical and electrosurgical system according to the present embodiment, ultrasonic output is combined with high-frequency output by controlling ultrasonic and high-frequency output timings, so that a treatment can be performed without reducing speed for incising tissue. Accordingly, a treatment on biological tissue can be smoothly performed and the range of surgical operations by the operator can be increased.

Third Embodiment

A third embodiment of the present invention will now be described with reference to FIGS. 15 to 18D. The fundamental structure of an ultrasonic-surgical and electrosurgical system according to the present embodiment is similar to that according to the first embodiment. A relay device 6C according to the present embodiment differs from the relay device 6 in that the device 6C further includes communication means for communicating with an ultrasonic surgical device.

The ultrasonic-surgical and electrosurgical system according to the present embodiment includes an ultrasonic surgical device 3C instead of the ultrasonic surgical device 3 in the first embodiment. The ultrasonic surgical device 3C includes communication means for communicating with the relay device 6C.

According to the present embodiment, before the ultrasonic surgical device 3C drives a handpiece 2 to generate ultrasonic vibration, a resonance frequency (resonance point) of an ultrasonic transducer 9 disposed in the handpiece 2 is searched for and the ultrasonic transducer 9 is then driven at the resonance point.

The third embodiment will now be described in detail below.

Figure 15:
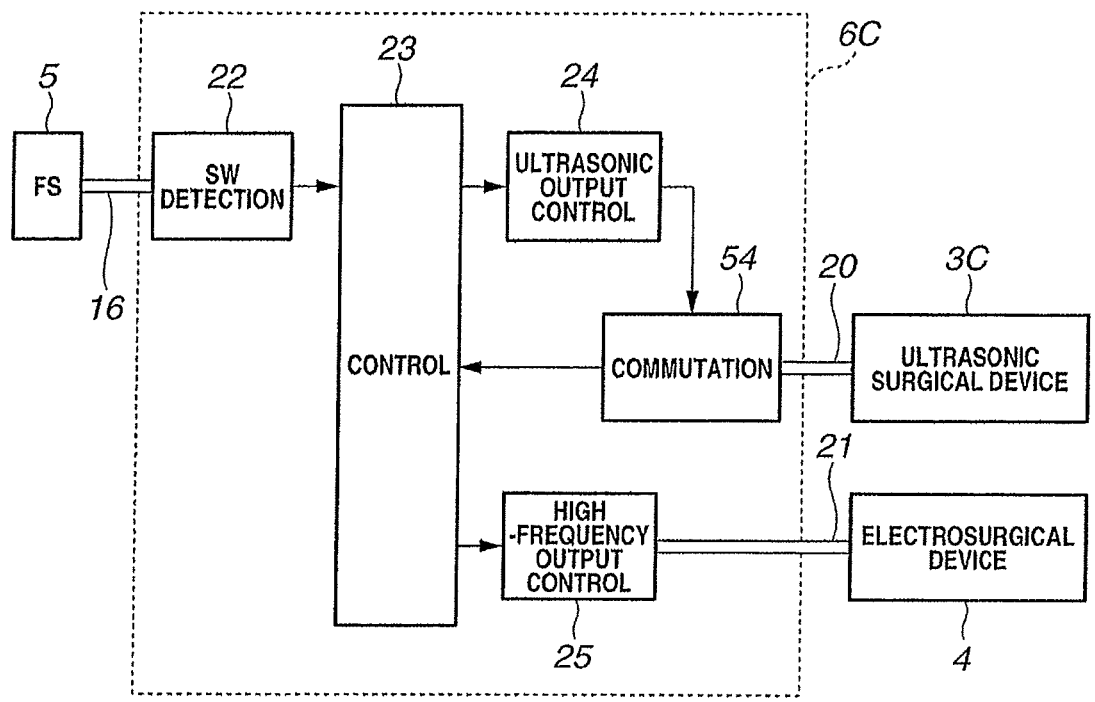
FIG. 15 is a block diagram showing the structure of a relay device according to a third embodiment of the present invention.

FIG. 15 shows the internal structure of the relay device 6C according to the present embodiment. The relay device 6C further includes a communication unit 54 in the relay device 6 according to the first embodiment.

Specifically, the relay device 6C includes a switch detection unit 22, a control unit 23, an ultrasonic output control unit 24, a high-frequency output control unit 25, and the communication unit 54 for communicating with a communication unit 55 included in the ultrasonic surgical device 3B.

In the relay device 6C, the communication unit 54 transmits an ultrasonic control signal output from the ultrasonic output control unit 24 to the communication unit 55 in the ultrasonic surgical unit 3C. In addition, the communication unit 54 receives a signal from the communication unit 55 and transfers the received signal to the control unit 23. The communication unit 54 of the relay device 6C is connected to the communication unit 55 in the ultrasonic surgical device 3C via an ultrasonic surgical device connecting cable 20 for the ultrasonic surgical device 3C.

Figure 16:
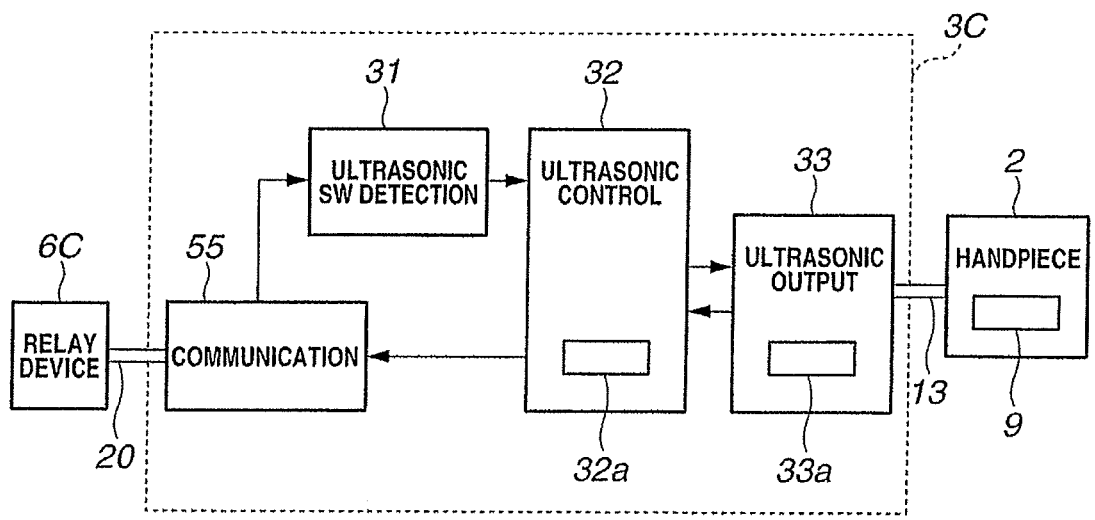
FIG. 16 is a block diagram illustrating the internal structure of an ultrasonic surgical device according to the third embodiment.

As described above, the ultrasonic-surgical and electrosurgical system according to the present embodiment includes the ultrasonic surgical device 3C shown in FIG. 16 instead of the ultrasonic surgical device 3 in the ultrasonic-surgical and electrosurgical system 1 shown in FIGS. 1 and 2.

The ultrasonic surgical device 3C is designed such that the communication unit 55 is added to the structure of the ultrasonic surgical device 3 shown in FIG. 4.

In other words, the ultrasonic surgical device 3C includes the communication unit 55, an ultrasonic switch detection unit 31, an ultrasonic control unit 32, and an ultrasonic output unit 33.

The communication unit 55 receives a signal indicative of the turn-on/off of a switch element 24a constituting the ultrasonic output control unit 24 from the relay device 6C via the ultrasonic surgical device connecting cable 20, the signal being output in accordance with the turn-on of a footswitch 5. The communication unit 55 transmits the received signal to the ultrasonic switch detection unit 31. The ultrasonic switch detection unit 31 supplies the signal to the ultrasonic control unit 32. The ultrasonic control unit 32 controls the ultrasonic output unit 33 to start the operation of searching for a resonance point.

The ultrasonic output unit 33, therefore, includes a frequency sweep section 33a for sweeping the frequency of an ultrasonic signal. The frequency sweep section 33a sweeps an ultrasonic signal frequency using an output signal of the ultrasonic control unit 32 as a trigger signal. The amplitude of an ultrasonic signal for resonance-point search is sufficiently smaller than that for treatment.

The ultrasonic output unit 33 outputs a signal from an output terminal thereof to the handpiece 2 via a handpiece cable 13 to drive the ultrasonic transducer 9.

In this instance, the ultrasonic output unit 33 transmits an ultrasonic signal (ultrasonic feedback signal), which is fed back via the ultrasonic handpiece cable 13, to the ultrasonic control unit 32. The ultrasonic control unit 32 includes a resonance-point detection section 32a for detecting or determining whether or not a resonance point.

In other words, the resonance-point detection section 32a in the ultrasonic control unit 32 monitors the impedance of a load or a change in current in the handpiece 2 connected to the output terminal of the ultrasonic output unit 33 via the ultrasonic handpiece cable 13.

In the occurrence of resonance, i.e., at the resonance point, for example, the minimum impedance is obtained. The resonance-point detection section 32a detects the minimum impedance, thus detecting the occurrence of resonance.

In the occurrence of resonance, the ultrasonic control unit 32 determines that the operation for searching for the resonance point is completed and allows the ultrasonic output section 33 to maintain the frequency at the resonance point. The ultrasonic control unit 32 also transmits a signal indicating the completion of the resonance-point search to the communication unit 55.

The frequency sweep section 33a and the resonance-point detection section 32a constitute a resonance-point search unit.

The communication unit 55 transmits the received completion signal to the control unit 23 in the relay device 6C through the ultrasonic surgical device connecting cable 20 and the communication unit 54. The other structure and arrangement of the system are similar to those of the system according to the first embodiment.

The operation of the ultrasonic-surgical and electrosurgical system according to the present embodiment will now be described with reference to a flowchart of FIG. 17.

When the relay device and ultrasonic-surgical and electrosurgical system according to the present embodiment enters an operating mode, the control unit 23 of the relay device 6C enters a standby mode waiting for the operation of pushing the footswitch 5 in step S21. When the footswitch 5 is pushed, in step S22, the switch detection unit 22 detects the turn-on of the footswitch 5 and transmits a switch-on signal to the control unit 23.

In step S23, when receiving the switch-on signal, the control unit 23 outputs an ultrasonic control signal to the ultrasonic output control unit 24 in accordance with a preset output control mode.

In step S24, the ultrasonic output control unit 24 turns on/off the switch element 24a in accordance with the ultrasonic control signal.

The ultrasonic output control unit 24 is connected to the communication unit 54 of the relay device 6C. The communication unit 54 is connected to the communication unit 55 in the ultrasonic surgical device 3C via the ultrasonic surgical device connecting cable 20.

In step S25, the communication unit 54 in the relay device 6C transmits a signal indicative of the turn-on/off of the switch element 24a to the communication unit 55.

In step S26, the communication unit 55 transmits the received on/off signal of the switch element 24a to the ultrasonic switch detection unit 31.

In step S27, the ultrasonic switch detection unit 31 detects the turn-on of the switch element 24a and transmits an ultrasonic switch-on signal to the ultrasonic control unit 32.

In step S28, the ultrasonic control unit 32 transmits an ultrasonic output signal for resonance-point search to the ultrasonic output unit 33 in accordance with the ultrasonic switch-on signal.

In step S29, the ultrasonic output unit 33 outputs an ultrasonic signal to the handpiece 2 connected thereto via the ultrasonic handpiece cable 13 in accordance with the received signal.

In step S30, the ultrasonic output unit 33 feeds back an ultrasonic feedback signal, which is returned from the handpiece 2 via the ultrasonic handpiece cable 13, to the ultrasonic control unit 32.

In step S31, the ultrasonic control unit 32 is in the standby mode waiting for the completion of resonance-point search while monitoring ultrasonic feedback signals.

When the resonance-point search is completed, the ultrasonic control unit 32 controls the ultrasonic output unit 33 to keep the frequency at the resonance point in step S32. In addition, the ultrasonic control unit 32 transmits a signal indicative of the completion of resonance-point search to the communication unit 55.

In this case, the ultrasonic output unit 33 outputs an ultrasonic driving signal with a preset amplitude. Alternatively, an ultrasonic signal may be output synchronously with a high-frequency output signal, which will be described below.

In step S33, the communication unit 55 transmits the received resonant-point search completion signal to the communication unit 54 in the relay device 6C via the ultrasonic surgical device connecting cable 20.

In step S34, the communication unit 54 transmits the received resonant-point search completion signal to the control unit 23.

In step S35, the control unit 23 receives the resonant-point search completion signal and then transmits a high-frequency output control signal to the high-frequency output control unit 25 in accordance with the preset output control mode.

In accordance with the set output control mode, an ultrasonic output value, ultrasonic-output start time, ultrasonic-output stop time, a high-frequency output mode (for coagulation or incision), high-frequency-output start time, and high-frequency-output stop time are changed.

In step S36, the high-frequency output control unit 25 turns on/off a switch element 25a in accordance with the received high-frequency output signal.

The high-frequency output control unit 25 is connected to the high-frequency switch detection unit 35 of the electrosurgical device 4 via a electrosurgical device connecting cable 21. The high-frequency switch detection unit 35, therefore, detects the turn-on/off of the switch element 25a as in the case of the turn-on/off of a footswitch 95 dedicated to the electrosurgical device. The high-frequency output control unit 25 allows the electrosurgical device 4 to output a high-frequency signal to the handpiece 2 via the high-frequency handpiece cable 15.

Figure 17:
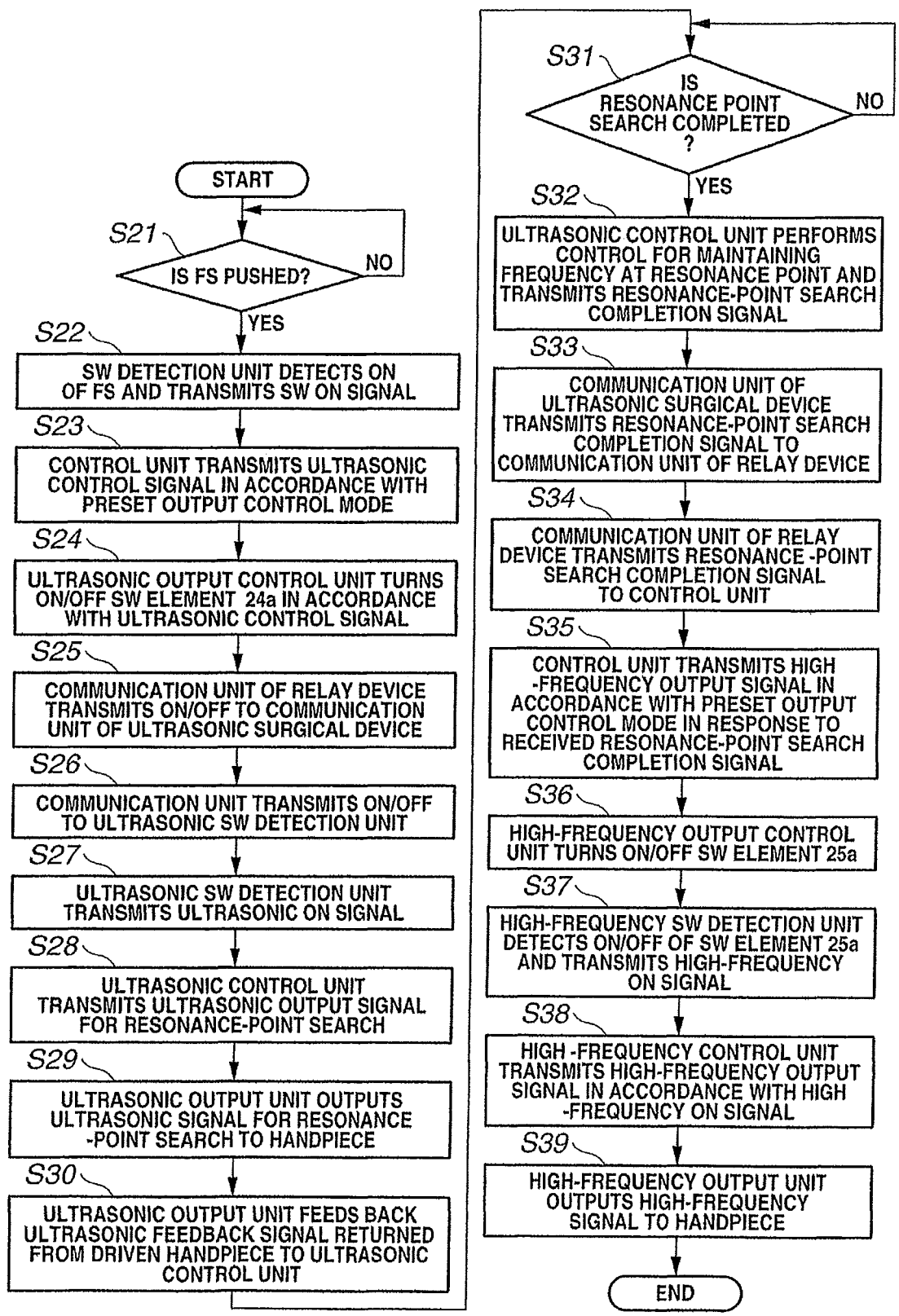
FIG. 17 is a flowchart of the operation of an ultrasonic-surgical and electrosurgical system according to the third embodiment.
Figure 18:
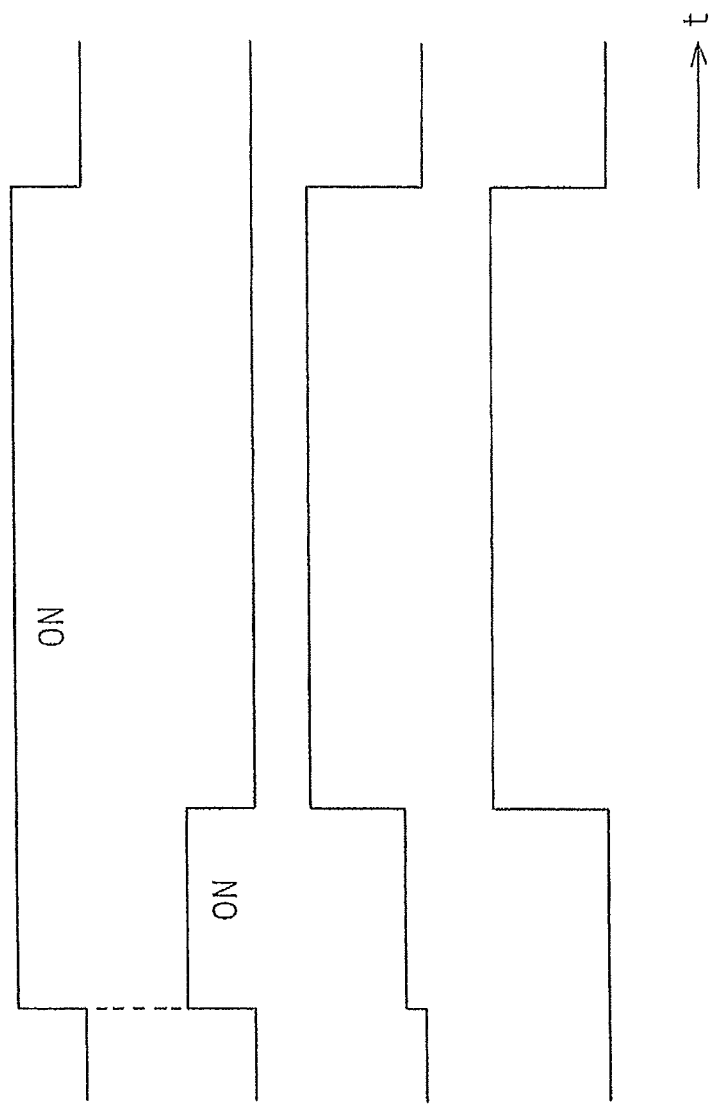
FIGS. 18A to 18D are timing diagrams of the operation according to the third embodiment.

The operation described with reference to FIG. 17 is shown using timing diagrams of FIGS. 18A to 18D.

Referring to FIG. 18A, when the footswitch 5 is turned on, the switch detection unit 22 detects turn-on timing, so that an ultrasonic switch-on signal is supplied to the ultrasonic control unit 32.

Referring to FIG. 18B, the ultrasonic control unit 32 transmits an ultrasonic output signal for resonance-point search to the ultrasonic output unit 33. Referring to FIG. 18C, the ultrasonic output unit 33 outputs an ultrasonic signal for resonance-point search to the handpiece 2.

At that time, the ultrasonic control unit 32 monitors the driving state of the handpiece 2 to determine whether the handpiece 2 vibrates at the resonance point, i.e., the resonance point is detected. When the resonance point is detected, the ultrasonic control unit 32 controls the amplitude of the ultrasonic signal output from the ultrasonic output unit 33 to a preset value.

At that time, the ultrasonic control unit 32 also transmits a signal indicative of the completion of resonance-point search to the control unit 23 in the relay device 6C. In response to the completion signal, the control unit 23 immediately transmits the completion signal to the electrosurgical device 4 through the high-frequency output control unit 25, so that the high-frequency output unit 37 outputs a high-frequency signal to the handpiece 2 as shown in FIG. 18D.

According to the present embodiment thus operating, as shown in FIGS. 18A to 18D, even when the operation of searching for the resonance point is performed after the turn-on of the footswitch 5, the ultrasonic driving signal and the high-frequency signal can be almost simultaneously output to the handpiece 2.

The present embodiment, therefore, solves the following problem: A high-frequency signal alone is output while the resonance point is searched for. Unfortunately, an operator uses only high-frequency current in a treatment during the search. According to the present embodiment, unintended preceding single output can be prevented, thus reducing the burden on the operator.

In the conventional ultrasonic surgical device of the foregoing related ultrasonic-surgical and electrosurgical system, if resonance-point search is performed in order to obtain set ultrasonic output, the associated electrosurgical device outputs high-frequency current preceding to the output of ultrasonic vibration from the ultrasonic surgical device, though the operator intends to simultaneously start outputs of both the devices.

Disadvantageously, the operator erroneously recognizes that both the devices supply energies while only the electrosurgical device outputs high-frequency current. Unfortunately, this leads to the burden on the operator during a surgery.

The present embodiment can solve the disadvantage as described above.

In the above description, it is assumed that the structure of the system according to the present embodiment is similar to that according to the first embodiment. The system may include a parameter switch 51 and a parameter-switch detection unit 52, which have been described in the second embodiment.

The present embodiment has the following advantages:

Outputs of both the ultrasonic surgical device and the electrosurgical device can be controlled by operating the single footswitch connected to the relay device. This arrangement enables the operator to readily perform switch operation during a treatment. In addition, since the number of switches is reduced, an operating room becomes clear.

The relay device detects the completion of resonance-point search performed by the ultrasonic surgical device. Although it takes some time to start output of the ultrasonic surgical device, the relay device can control the electrosurgical device to start output almost simultaneously with the output of the ultrasonic surgical device. Advantageously, a treatment can be performed more effectively than the conventional case where high-frequency output precedes ultrasonic output.

Fourth Embodiment

Figure 19:
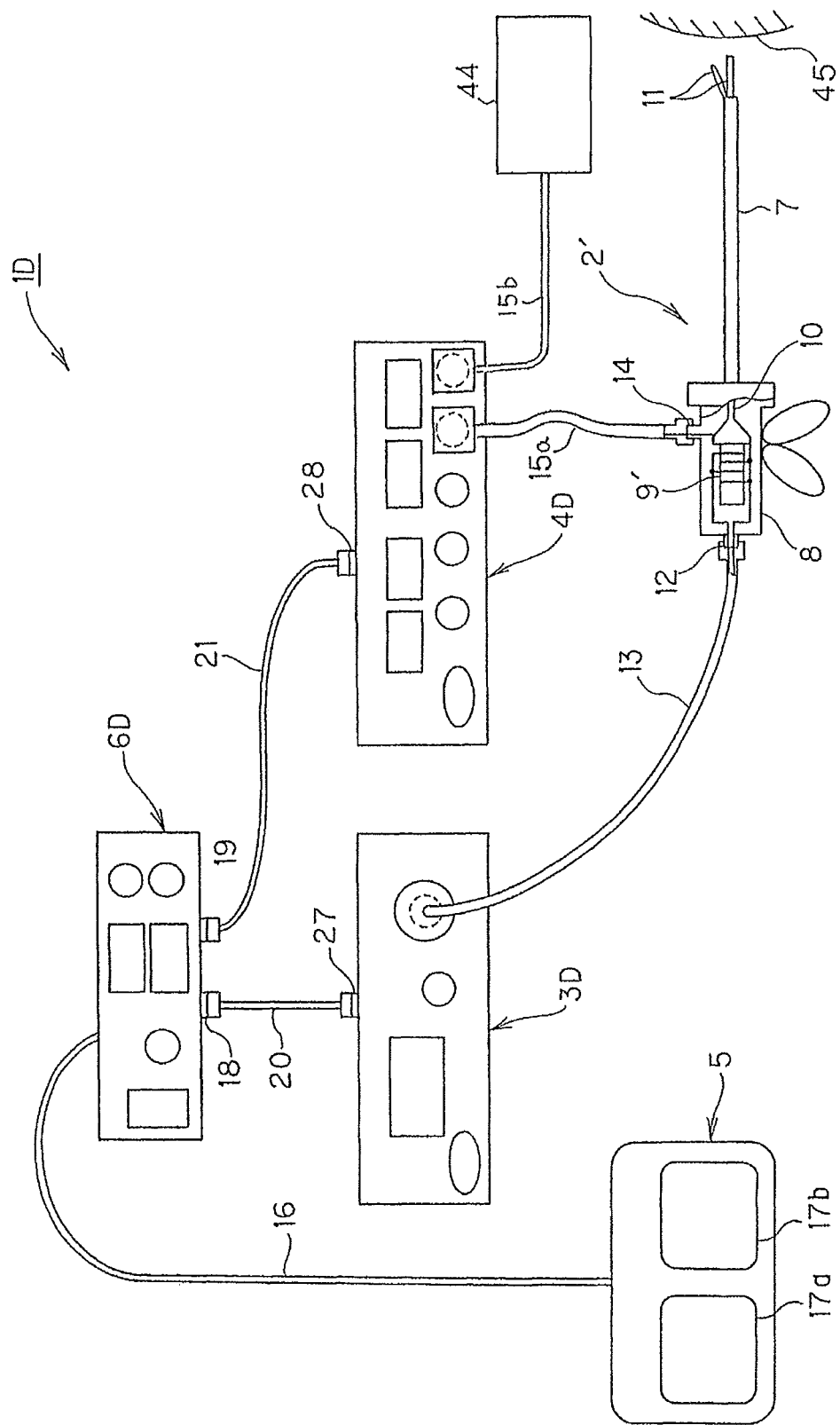
FIG. 19 is an external view of an ultrasonic-surgical and electrosurgical system according to a fourth embodiment of the present invention.

A fourth embodiment of the present invention will now be described with reference to FIGS. 19 to 21. FIG. 19 shows the structure of an ultrasonic-surgical and electrosurgical system 1D including a relay device 6D according to the fourth embodiment.

The ultrasonic-surgical and electrosurgical system 1D includes a handpiece 2', an ultrasonic surgical device 3D, an electrosurgical device 4D, a footswitch 5, and the relay device 6D.

As for the footswitch 5, a foot switch 94 dedicated to the ultrasonic surgical device, a footswitch 95 dedicated to the electrosurgical device, or a footswitch dedicated to the relay device may be used. The relay device 6D is connected to a footswitch connector 27 provided for the ultrasonic surgical device 4D via a ultrasonic surgical device connecting cable 20 for the device 3 and is also connected to a footswitch connector 28 provided for the electrosurgical device 4D via a electrosurgical device connecting cable 21 for the device 4D in a manner similar to the first embodiment.

The handpiece 2' is connected to the ultrasonic surgical device 3D via an ultrasonic handpiece cable 13 and is also connected to the electrosurgical device 4D via a handpiece cable 15a for high-frequency power supply.

Referring to FIG. 19, the handpiece 2' is a monopolar type that is different from the bipolar type of the foregoing handpiece 2.

In this case, the handpiece cable 15a is connected to a positive output terminal of the electrosurgical device 4D. One end of a handpiece cable 15b, serving as a high-frequency current return path, is connected to a negative output terminal of the electrosurgical device 4D. The other end of the handpiece cable 15b is connected to a grounding pad 44. The grounding pad 44 is put on, for example, the buttock of a patient so that the contact area is large.

An ultrasonic transducer 9' according to the present embodiment differs from the foregoing ultrasonic transducer 9 in size. Therefore, an ultrasonic output level and an output waveform of the ultrasonic transducer 9' used for ultrasonic treatment are different from those of the ultrasonic transducer 9.

A hand switch may be used instead of the footswitch 5.

Figure 20:
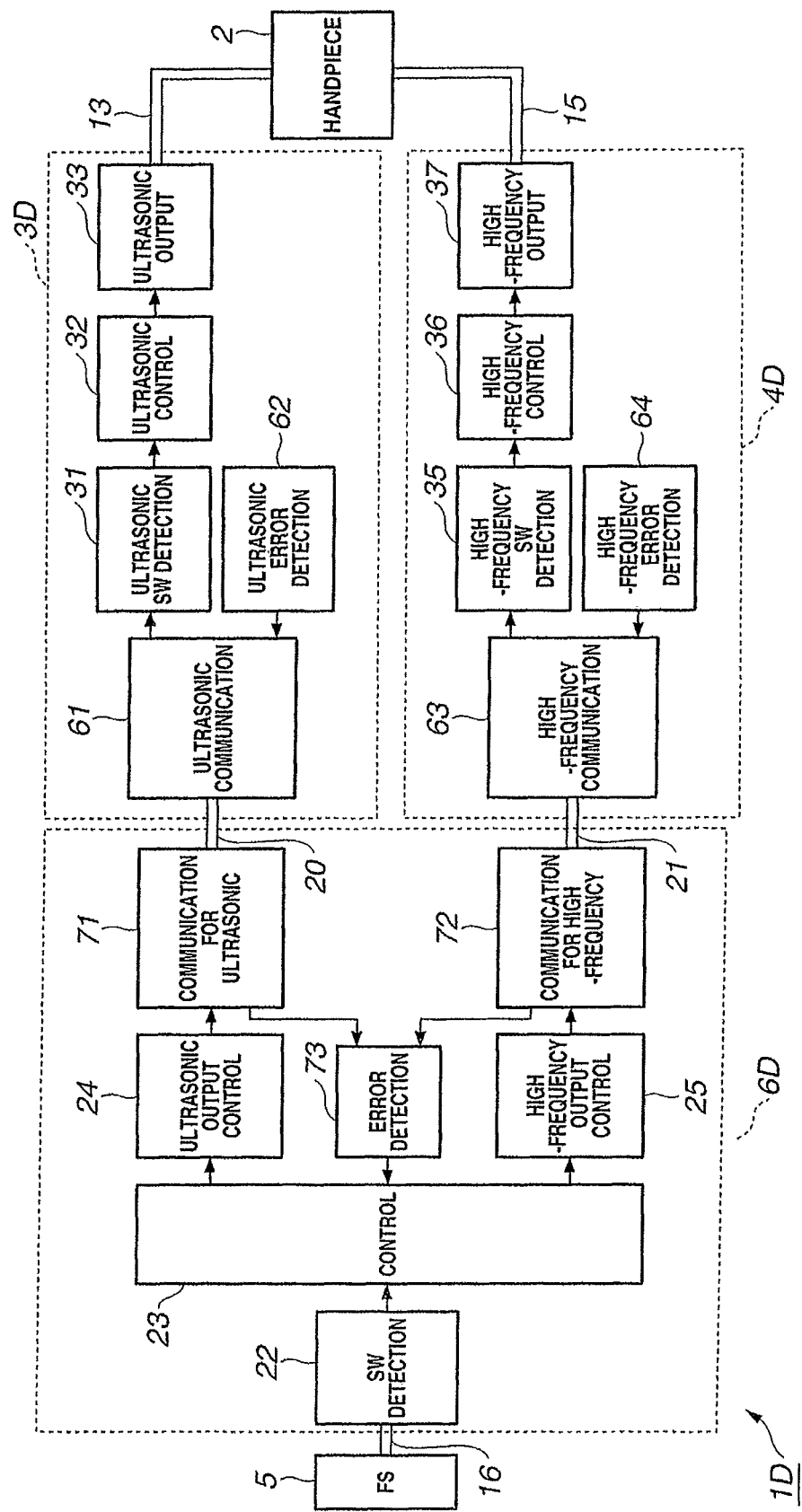
FIG. 20 is a block diagram illustrating the internal structure of the ultrasonic-surgical and electrosurgical system according to the fourth embodiment.
Figure 21:
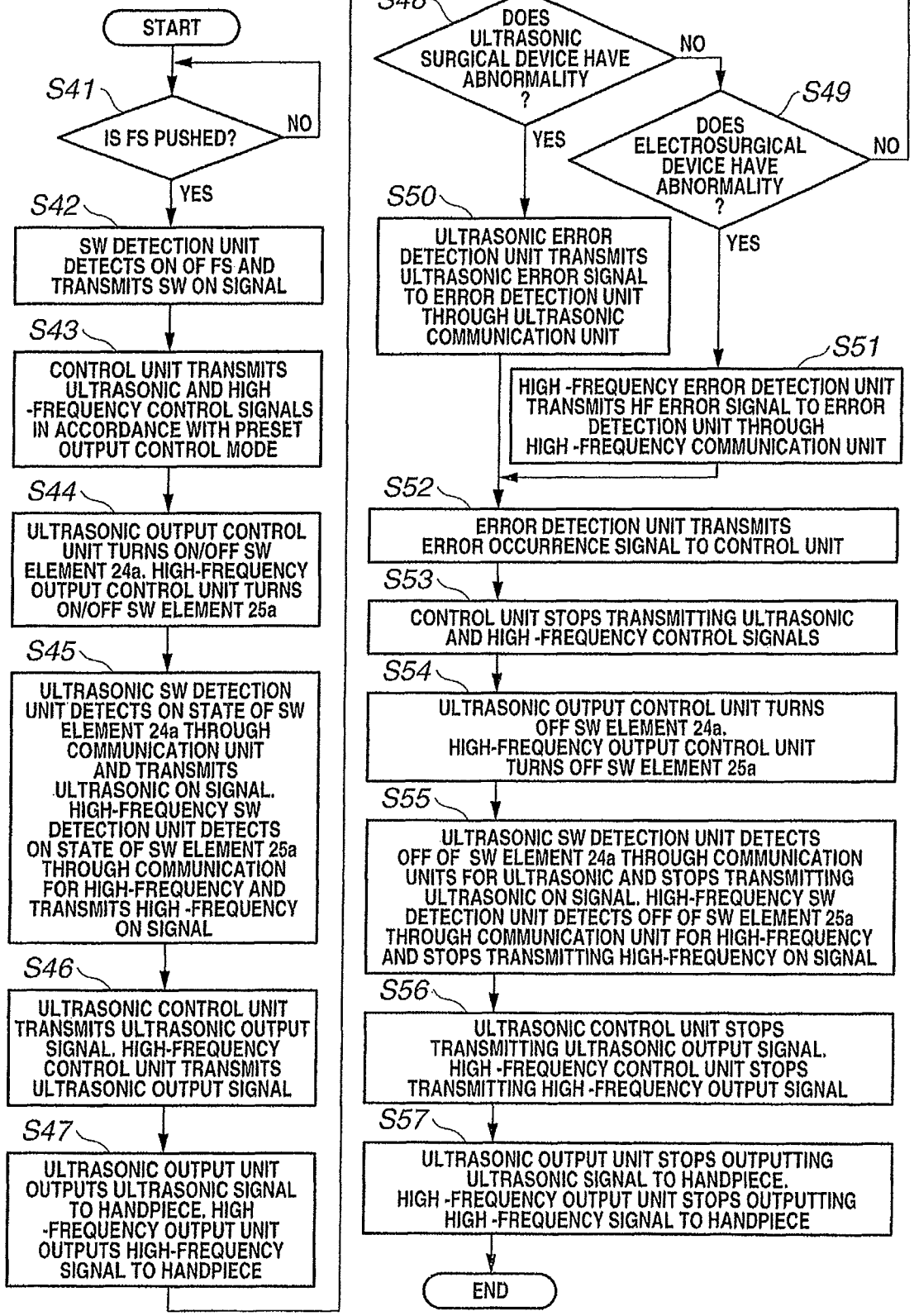
FIG. 21 is a flowchart of the operation of the ultrasonic-surgical and electrosurgical system according to the fourth embodiment.

FIG. 20 shows the internal structure of the present embodiment. The ultrasonic surgical device 3D includes an ultrasonic communication unit 61, an ultrasonic switch detection unit 31, an ultrasonic control unit 32, an ultrasonic output unit 33, and an ultrasonic error detection unit 62. The ultrasonic communication unit 61 communicates with the relay device 6D connected via the ultrasonic surgical device connecting cable 20. The ultrasonic switch detection unit 31 detects the start of ultrasonic output. The ultrasonic control unit 32 controls the ultrasonic output. The ultrasonic output unit 33 outputs an ultrasonic driving signal to the handpiece 2 connected via the ultrasonic handpiece cable 13. The ultrasonic error detection unit 62 detects an abnormality (error) of the ultrasonic surgical device 3D.

The electrosurgical device 4D includes a high-frequency communication unit 63, a high-frequency switch detection unit 35, a high-frequency control unit 36, a high-frequency output unit 37, and a high-frequency error detection unit 64. The high-frequency communication unit 63 communicates the relay device 6D connected via the electrosurgical device connecting cable 21. The high-frequency switch detection unit 35 detects the start of high-frequency output. The high-frequency control unit 36 controls the high-frequency output. The high-frequency output unit 37 outputs a high-frequency signal to the handpiece 2' connected via the high-frequency handpiece cable 15. The high-frequency error detection unit 64 detects an abnormality of the electrosurgical device 4D.

The relay device 6D includes a switch detection unit 22, a control unit 23, a communication unit 71 for ultrasonic, an ultrasonic output control unit 24, a communication unit 72 for high frequency, a high-frequency output control unit 25, and an error detection unit 73. The switch detection unit 22 detects the operation on the footswitch 5. The control unit 23 controls an output mode and an output timing. The communication unit 71 for ultrasonic communicates with the ultrasonic communication unit 61 of the ultrasonic surgical device 3D through the ultrasonic surgical device connecting cable 20. The ultrasonic output control unit 24 controls the ultrasonic output. The communication unit 72 for high-frequency communicates with the high-frequency communication unit 63 of the electrosurgical device 4D through the electrosurgical device connecting cable 21. The high-frequency output control unit 25 controls the high-frequency output. The error detection unit 73 detects an abnormality of each of the ultrasonic surgical device 3D and the electrosurgical device 4D.

The ultrasonic communication unit 61 in the ultrasonic surgical device 3D, the high-frequency communication unit 63 in the electrosurgical device 4D, and the communication units 71 for ultrasonic and 72 for high-frequency in the relay device 6D each output a received signal. In other words, the respective communication units relay signals.

The ultrasonic switch detection unit 31 in the ultrasonic surgical device 3D is substantially connected to the ultrasonic output control unit 24 in the relay device 6D via the ultrasonic surgical device connecting cable 20.

The high-frequency switch detection unit 35 in the electrosurgical device 4D is substantially connected to the high-frequency output control unit 25 in the relay device 6D via the electrosurgical device connecting cable 21.

Accordingly, the ultrasonic switch detection unit 31 in the ultrasonic surgical device 3D can detect the turn-on/off of a switch element 24a, constituting the ultrasonic output control unit 24 in the relay device 6D, as in the case of that of the footswitch 94 in a manner similar to the first embodiment. Similarly, the high-frequency switch detection unit 35 in the electrosurgical device 4D can detect the turn-on/off of a switch element 25a, constituting the high-frequency output control unit 25 in the electrosurgical device 4D, as in the case of that of the footswitch 95.

The operation of the system according to the present embodiment will now be described with reference to a flowchart of FIG. 21.

When the ultrasonic-surgical and electrosurgical system 1D is powered on and the system enters an operating state, the switch detection unit 22 enters a standby mode waiting for the operation of pushing the footswitch 5 in step S41.

When the footswitch 5 is pushed, in step S42, the switch detection unit 22 detects the turn-on of the footswitch 5 and transmits a switch-on signal to the control unit 23.

In step S43, in response to the switch-on signal, the control unit 23 outputs an ultrasonic control signal and a high-frequency control signal to the ultrasonic output control unit 24 and the high-frequency output control unit 25 in a preset output control mode, respectively. The preset output control mode includes parameters, e.g., an ultrasonic output value, ultrasonic-output start time, ultrasonic-output stop time, a high-frequency power mode for coagulation or incision, high-frequency-output start time, and high-frequency-output stop time.

In step S44, the ultrasonic output control unit 24 turns on/off the switch element 24a in accordance with the received ultrasonic control signal.

The high-frequency output control unit 25 turns on/off the switch element 25a in accordance with the received signal.

The communication unit 71 for ultrasonic of the relay device 6D transmits information indicating the turn-on/off of the switch element 24a to the ultrasonic communication unit 61 of the ultrasonic surgical device 3D through the ultrasonic surgical device connecting cable 20. The ultrasonic switch detection unit 31 detects the turn-on/off of the switch element 24a through the ultrasonic communication unit 61.

In step S45, when detecting the on state of the switch element 24a, the ultrasonic switch detection unit 31 transmits an ultrasonic switch-on signal to the ultrasonic control unit 32.

The communication unit 72 for high-frequency of the relay device 6D transmits information indicating the turn-on/off of the switch element 25a to the high-frequency communication unit 63 of the electrosurgical device 4D via the electrosurgical device connecting cable 21. Then, the high-frequency switch detection unit 35 detects the turn-on/off of the switch element 25a.

When detecting the on state of the switch element 25a, the high-frequency switch detection unit 35 outputs a high-frequency switch-on signal to the high-frequency control unit 36.

In step S46, the ultrasonic control unit 32 outputs an ultrasonic output signal to the ultrasonic output unit 33.

In addition, the high-frequency control unit 36 outputs a high-frequency output signal to the high-frequency output unit 37.

In step S47, the ultrasonic output unit 33 outputs an ultrasonic signal to the handpiece 2' connected via the ultrasonic handpiece cable 13 in accordance with the received ultrasonic output signal.

In addition, the high-frequency output unit 37 outputs a high-frequency signal to the handpiece 2' connected via the cable 15a in accordance with the received high-frequency output signal.

In this case, in step S48, the ultrasonic error detection unit 62 monitors whether the ultrasonic surgical device 3D has an abnormality. In addition, in step S49, the high-frequency error detection unit 64 monitors whether the electrosurgical device 4D has an abnormality.

Specifically, in step S48, the ultrasonic error detection unit 62 determines whether the ultrasonic surgical device 3D has an abnormality. If NO, the high-frequency error detection unit 64 determines whether the electrosurgical device 4D has an abnormality. If NO, the operation is returned to step S48.

On the other hand, if the ultrasonic error detection unit 62 detects the abnormality, the operation proceeds to step S50. If the high-frequency error detection unit 64 detects the abnormality, the operation proceeds to step S51.

In step S50, the ultrasonic error detection unit 62 generates an ultrasonic error signal and transmits the signal through the ultrasonic communication unit 61 to the communication unit 71 for ultrasonic in the relay device 6D connected via the ultrasonic surgical device connecting cable 20. The signal is further transmitted to the error detection unit 73 through the communication unit 71 for ultrasonic.

In step S51, the high-frequency error detection unit 64 generates a high-frequency error signal and transmits the signal through the high-frequency communication unit 63 to the communication unit 72 for high-frequency in the relay device 6D connected via the electrosurgical device connecting cable 21. The signal is further transmitted to the error detection unit 73 through the communication unit 72 for high-frequency.

In step S52, the error detection unit 73 transmits an error detection signal to the control unit 23 in response to the ultrasonic or high-frequency error signal.

In step S53, when receiving the error detection signal, the control unit 23 stops transmitting the ultrasonic control signal and the high-frequency control signal to the ultrasonic output control unit 24 and the high-frequency output control unit 25.

In step S54, the ultrasonic output control unit 24 turns off the switch element 24a. The high-frequency output control unit 25 turns off the switch element 25a.

In step S55, the ultrasonic switch detection unit 31 in the ultrasonic surgical device 3D detects the turn-off of the switch element 24a in the ultrasonic output control unit 24 through the communication unit 71 for ultrasonic of the relay device 6D and the ultrasonic communication unit 61. The ultrasonic switch detection unit 31 stops transmitting the ultrasonic switch-on signal to the ultrasonic control unit 32.

Similarly, the high-frequency switch detection unit 35 in the electrosurgical device 4D detects the turn-off of the switch element 25a in the high-frequency output control unit 25 through the communication unit 72 for high-frequency in the relay device 6D and the high-frequency communication unit 63. The high-frequency switch detection unit 35 stops transmitting the high-frequency switch-on signal to the high-frequency control unit 36.

In step S56, the ultrasonic control unit 32 stops transmitting the ultrasonic output signal to the ultrasonic output unit 33.

In addition, the high-frequency control unit 36 stops transmitting the high-frequency output signal to the high-frequency output unit 37.

In step S57, the ultrasonic output unit 33 and the high-frequency output unit 37 stop transmitting the ultrasonic and high-frequency signals to the handpiece 2'.

In accordance with the present embodiment, if the occurrence of an abnormality in either the ultrasonic surgical device 3D or the electrosurgical device 4D is detected, the output of the ultrasonic and high-frequency signals to the handpiece 2' is stopped. This results in an improvement of the treatment reliability of the ultrasonic-surgical and electrosurgical system 1D.

The present embodiment has the following advantages:

Outputs of both the ultrasonic surgical device 3D and the electrosurgical device 4D can be controlled by operating the single footswitch 5 connected to the relay device 6D. This arrangement enables the operator to readily manipulate switches during a treatment. In addition, since the number of switches is reduced, an operating room becomes clear.

If an abnormality occurs in either the ultrasonic surgical device 3D or the electrosurgical device 4D, outputs of both the devices can be stopped through the relay device 6D, thus increasing the reliability of the present system.

Fifth Embodiment

Figure 22:
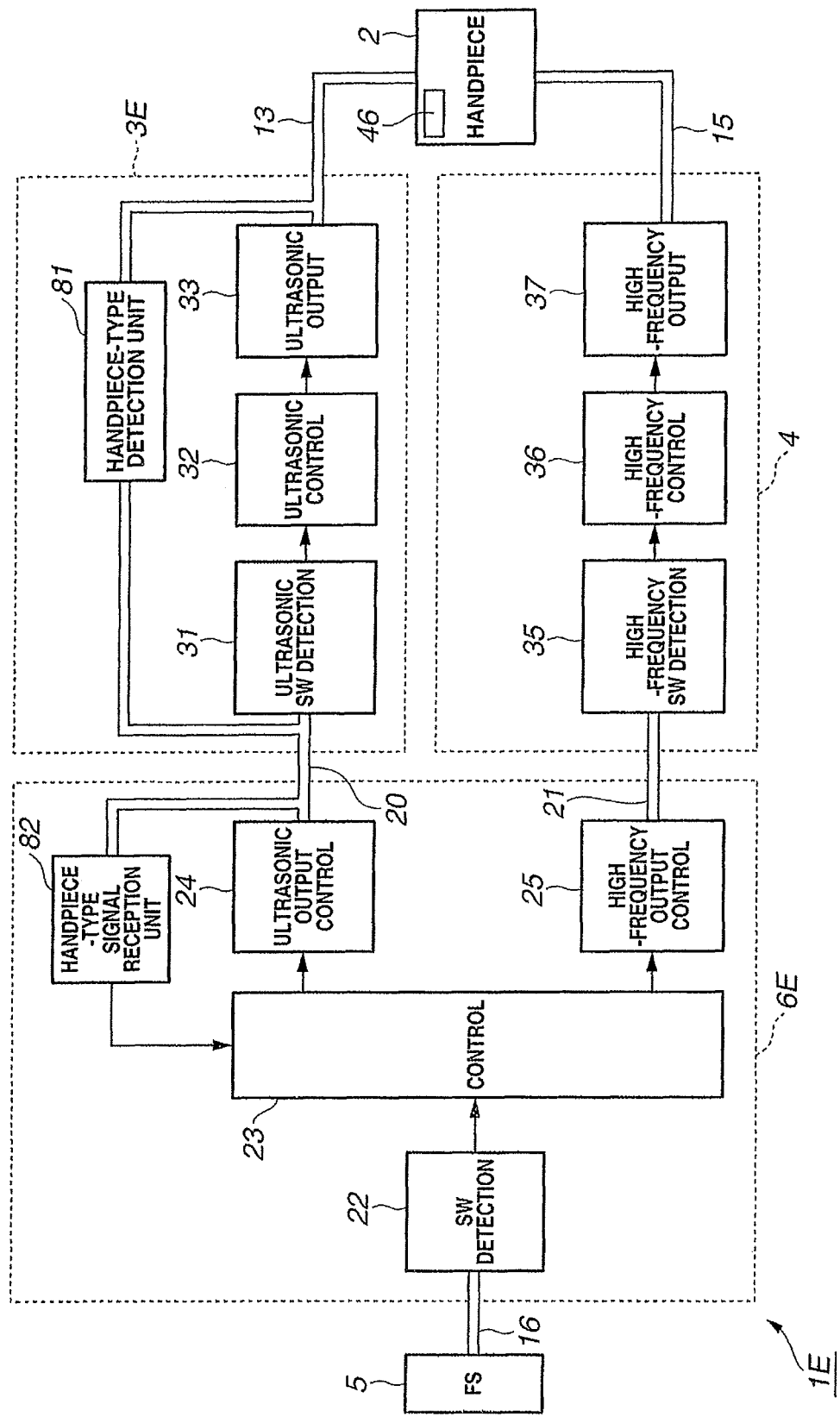
FIG. 22 is a block diagram showing the internal structure of an ultrasonic-surgical and electrosurgical system according to a fifth embodiment of the present invention.
Figure 23:
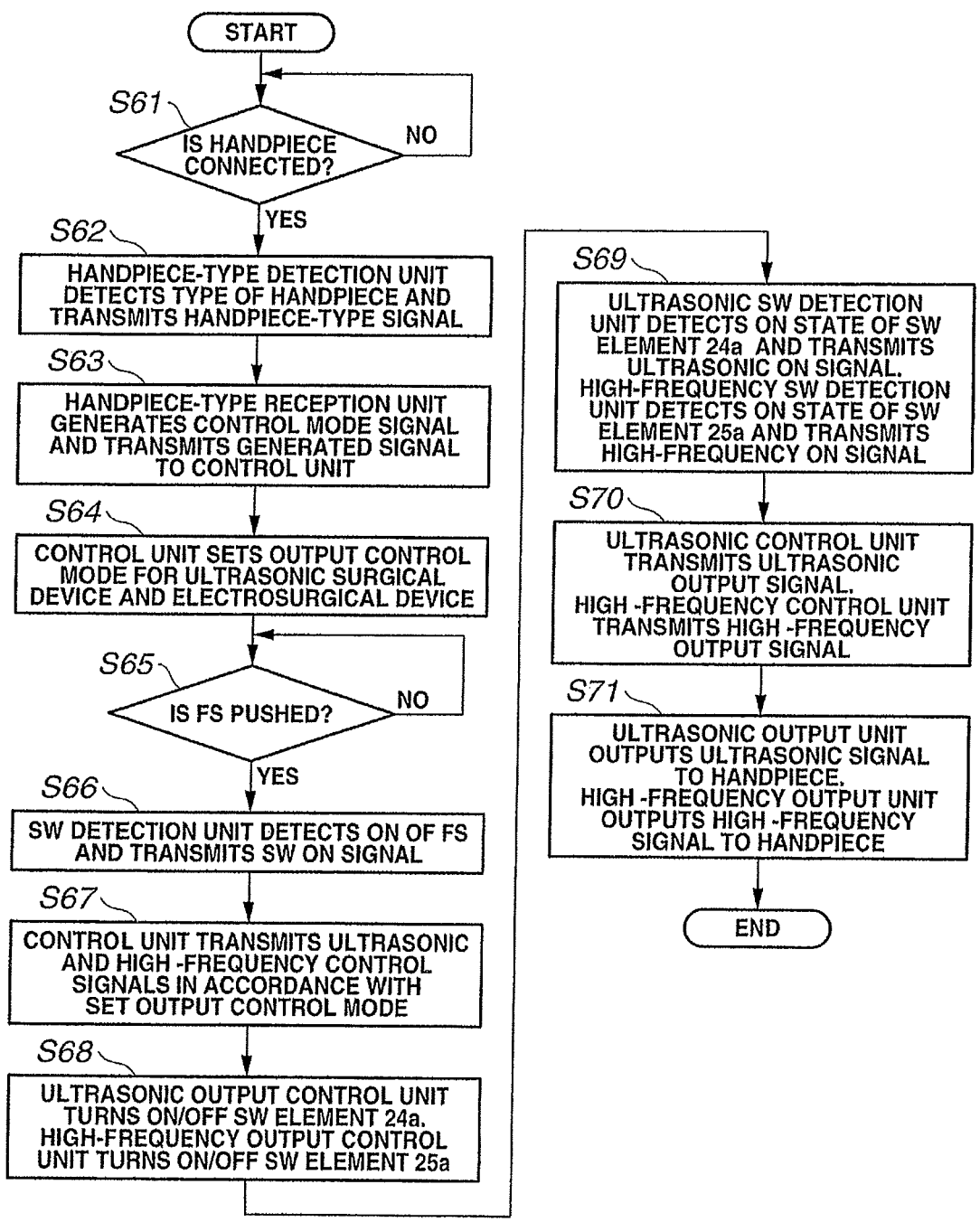
FIG. 23 is a flowchart of the operation of the ultrasonic-surgical and electrosurgical system according to the fifth embodiment.

A fifth embodiment of the present invention will now be described with reference to FIGS. 22 and 23. FIG. 22 shows the internal structure of an ultrasonic-surgical and electrosurgical system 1E including a relay device 6E according to the fifth embodiment.

In accordance with the present embodiment, the ultrasonic-surgical and electrosurgical system 1E is compatible with different types of handpieces 2 and 2'. Referring to FIG. 22, the handpiece 2 is connected to both of an ultrasonic surgical device 3E and an electrosurgical device 4E. Alternatively, the different type of handpiece 2' can be connected to the devices 3E and 4E, as described in the fourth embodiment.

As compared to the ultrasonic-surgical and electrosurgical system 1 according to the first embodiment, the ultrasonic-surgical and electrosurgical system 1E further includes other components: The ultrasonic surgical device 3E includes handpiece-type detecting means. The relay device 6E includes receiving means (signal relay means) for receiving a signal indicative of the handpiece type detected by the handpiece-type detecting means and transferring the signal to a control unit 23.

The relay device 6E includes a switch detection unit 22, the control unit 23, an ultrasonic output control unit 24, a high-frequency output control unit 25, and a handpiece-type signal reception 82. The switch detection unit 22 detects the operation on a footswitch 5 connected to the relay device 6E. The control unit 23 controls an output mode and an output timing of each of the ultrasonic surgical device 3E and the electrosurgical device 4E. The ultrasonic output control unit 24 controls ultrasonic output. The high-frequency output control unit 25 controls high-frequency output. The handpiece-type signal reception 82 receives a signal indicative of the type of the connected handpiece, the signal being transmitted from the ultrasonic surgical device 3E.

The ultrasonic surgical device 3E includes an ultrasonic switch detection unit 31, an ultrasonic control unit 32, an ultrasonic output unit 33, and a handpiece-type detection unit 81. The ultrasonic control unit 32 controls ultrasonic output. The ultrasonic output unit 33 outputs an ultrasonic signal to the handpiece 2 or 2' (hereinafter, represented by reference numeral 2) connected via an ultrasonic handpiece cable 13. The handpiece-type detection unit 81 detects a connection of handpiece 2 and the type of the handpiece 2.

The electrosurgical device 4E includes a high-frequency switch detection unit 35, a high-frequency control unit 36, and a high-frequency output unit 37.

According to the present embodiment, the ultrasonic-surgical and electrosurgical system 1E can detect the operation on the footswitch 5 and allow the relay device 6E to transmit output control signals to the ultrasonic surgical device 3E and the electrosurgical device 4E in a manner similar to the first embodiment.

When the handpiece 2 is connected to the ultrasonic surgical device 3E, the handpiece-type detection unit 81 in the ultrasonic surgical device 3E detects the type of the connected handpiece 2 and transmits a signal indicative of the type of the handpiece to the handpiece-type signal reception 82 in the relay device 6E connected via an ultrasonic surgical device connecting cable 20.

The handpiece 2 includes, for example, an ID unit 46 capable of identifying the type of the handpiece 2. The ID unit 46 comprises an ROM and the like which stores a resistance and identification information. The handpiece-type detection unit 81 outputs information stored in the ID unit 46 as a handpiece-type signal.

The handpiece-type signal reception 82 transmits a control mode signal to the control unit 23 in accordance with the received handpiece-type signal.

In accordance with the received control mode signal, the control unit 23 automatically sets an output mode and an output timing of each of the ultrasonic surgical device 3E and the electrosurgical device 4E so that the modes and timings are suitable for the type of the connected handpiece 2.

According to the present embodiment, the present system can be operated in the output control mode suitable for the type of the connected handpiece 2.

The operation of the system according to the present embodiment will now be described with reference to a flowchart of FIG. 23.

When the ultrasonic-surgical and electrosurgical system 1E is powered on and starts to operate, in step S61, the handpiece-type detection unit 81 in the ultrasonic surgical device 3E enters a standby mode waiting for the operation of connecting the handpiece 2 to the ultrasonic surgical device 3E.

When the handpiece 2 is connected to the device 3E, in step S62, the handpiece-type detection unit 81 detects the type of the connected handpiece 2 and transmits a handpiece-type signal to the relay device 6E.

In step S63, the handpiece-type signal reception 82 in the relay device 6E generates a control mode signal suitable for the type of the connected handpiece 2 on the basis of the received handpiece-type signal and transmits the generated signal to the control unit 23.

In step S64, the control unit 23 sets an output control mode for the ultrasonic surgical device 3E and the electrosurgical device 4E on the basis of the type of the connected handpiece 2 in accordance with the received control mode signal.

In step S65, the switch detection unit 22 enters a standby mode waiting for the operation of pushing the footswitch 5.

When the footswitch 5 is pushed, in step S66, the switch detection unit 22 detects the turn-on of the footswitch 5 and transmits a switch-on signal to the control unit 23.

In step S67, in response to the switch-on signal, the control unit 23 transmits an ultrasonic control signal and a high-frequency control signal to the ultrasonic output control unit 24 and the high-frequency output control unit 25 in accordance with the set output control mode, respectively.

In step S68, the ultrasonic output control unit 24 turns on/off a switch element 24a in accordance with the received ultrasonic control signal. In addition, the high-frequency output control unit 25 turns on/off a switch element 25a in accordance with the received high-frequency control signal.

In step S69, the ultrasonic switch detection unit 31 in the ultrasonic surgical device 3E detects the ON state of the switch element 24a of the ultrasonic output control unit 24 in the relay device 6E connected via the ultrasonic surgical device connecting cable 20 and transmits an ultrasonic switch-on signal to the ultrasonic control unit 32.

The high-frequency switch detection unit 35 in the electrosurgical device 4E detects the ON state of the switch element 25a of the high-frequency output control unit 25 in the relay device 6E connected via the electrosurgical device connecting cable 21 and transmits a high-frequency switch-on signal to the high-frequency control unit 36.

In step S70, the ultrasonic control unit 32 transmits an ultrasonic output signal to the ultrasonic output unit 33 in accordance with the ultrasonic switch-on signal.

In addition, the high-frequency control unit 36 transmits a high-frequency output signal to the high-frequency output unit 37 in accordance with the high-frequency switch-on signal.

In step S71, the ultrasonic output unit 33 outputs an ultrasonic signal to the handpiece 2 connected via the ultrasonic handpiece cable 13.

In addition, the high-frequency output unit 37 outputs a high-frequency signal to the handpiece 2 connected via the high-frequency handpiece cable 15.

According to the present embodiment, the control mode for ultrasonic output and high-frequency output can be automatically set in accordance with the type of connected handpiece 2 without manipulation by an operator.

Again referring to FIG. 22, the handpiece-type detection unit 81 is built in the ultrasonic surgical device 3E. The handpiece-type detection unit 81 may be included in the electrosurgical device 4E. In this case, the handpiece-type signal reception 82 in the relay device 6E may be connected to the electrosurgical device connecting cable 21.

The present embodiment has the following advantages:

Outputs of both the ultrasonic surgical device 3E and the electrosurgical device 4E can be controlled by operating the single footswitch 5 connected to the relay device 6E. This arrangement enables the operator to readily manipulate switches during a treatment.

In addition, since the number of switches is reduced, an operating room becomes clear.

According to the present embodiment, the relay device 6E can control outputs of both the ultrasonic surgical device 3E and the electrosurgical device 4E in accordance with output modes and output timings suitable for the type of handpiece connected.

The present embodiment can save the operator from setting or changing the output modes and output timings each time the handpiece 2 is changed.

Sixth Embodiment

Figure 25:
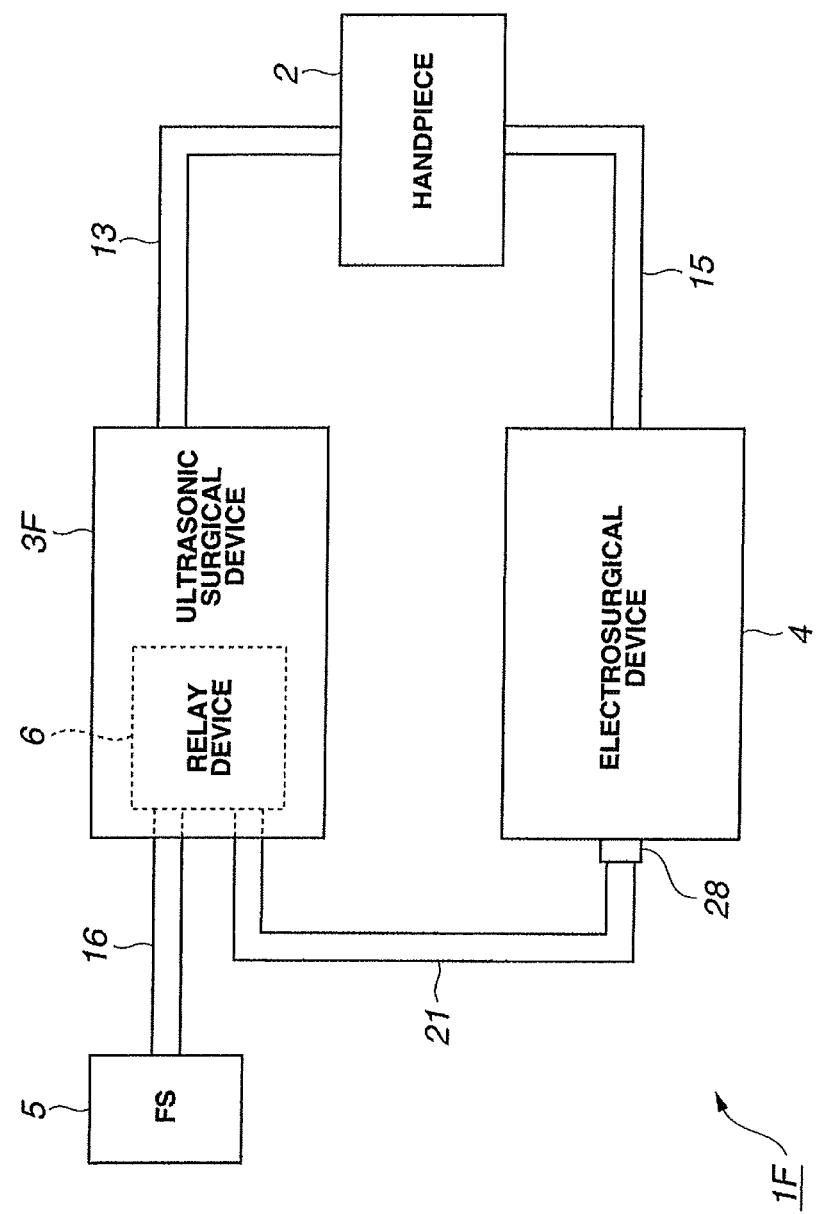
FIG. 25 is a block diagram illustrating the whole structure of an ultrasonic-surgical and electrosurgical system according to a sixth embodiment of the present invention.

Next, a sixth embodiment of the present invention will be described with reference to FIGS. 25 and 26. FIG. 25 shows an ultrasonic-surgical and electrosurgical system 1F according to the sixth embodiment of the present invention. In the above-described first to fifth embodiments, the relay devices 6, 6B to 6E are provided independently of the ultrasonic surgical devices 3, 3C, 3D, and 3E, and the electrosurgical devices 4, 4C, and 4D.

The ultrasonic-surgical and electrosurgical system 1F shown in FIG. 25 differs from the ultrasonic-surgical and electrosurgical system 1 according to the first embodiment shown in FIG. 1 in that the relay device 6 is built in the ultrasonic surgical device 3, for example.

The ultrasonic-surgical and electrosurgical system 1F includes: the handpiece 2; an ultrasonic surgical device 3F in which the relay device 6 controlling output modes and output timings is built; an electrosurgical device 4; and the footswitch 5 connected to the ultrasonic surgical device 3F. Note that, since more detailed structures of the handpiece 2 and the like have been described in the first embodiment, descriptions thereof will be omitted. Furthermore, also the detailed structures of other components will be omitted.

The ultrasonic handpiece cable 13 of the handpiece 2 is connected to an output connector of the ultrasonic surgical device 3F, and the high-frequency handpiece cable 15 is connected to an output connector of the electrosurgical device 4.

In addition, the footswitch 5 is connected to the relay device 6 disposed inside of the ultrasonic surgical device 3F through the footswitch cable 16.

In this case, the footswitch cable 16 may include a footswitch cable unit which connects the footswitch 5 and the ultrasonic surgical device 3F, and a connecting cable unit which is connected to one end of the footswitch cable unit to connect the footswitch cable unit to the relay device 6 disposed inside of the ultrasonic surgical device 3F.

In addition, the relay device 6 disposed inside of the ultrasonic surgical device 3F is connected to the high-frequency connector 28 of the electrosurgical device 4 through the electrosurgical device connecting cable 21. Also in this case, the electrosurgical device connecting cable 21 may include an electrosurgical device connecting cable unit which connects the high-frequency connector 28 of the electrosurgical device 4 and the ultrasonic surgical device 3F, and a connecting cable unit which is connected to one end of the electrosurgical device connecting cable unit to connect the electrosurgical device connecting cable to the relay device 6 disposed inside of the ultrasonic surgical device 3F.

Figure 26:
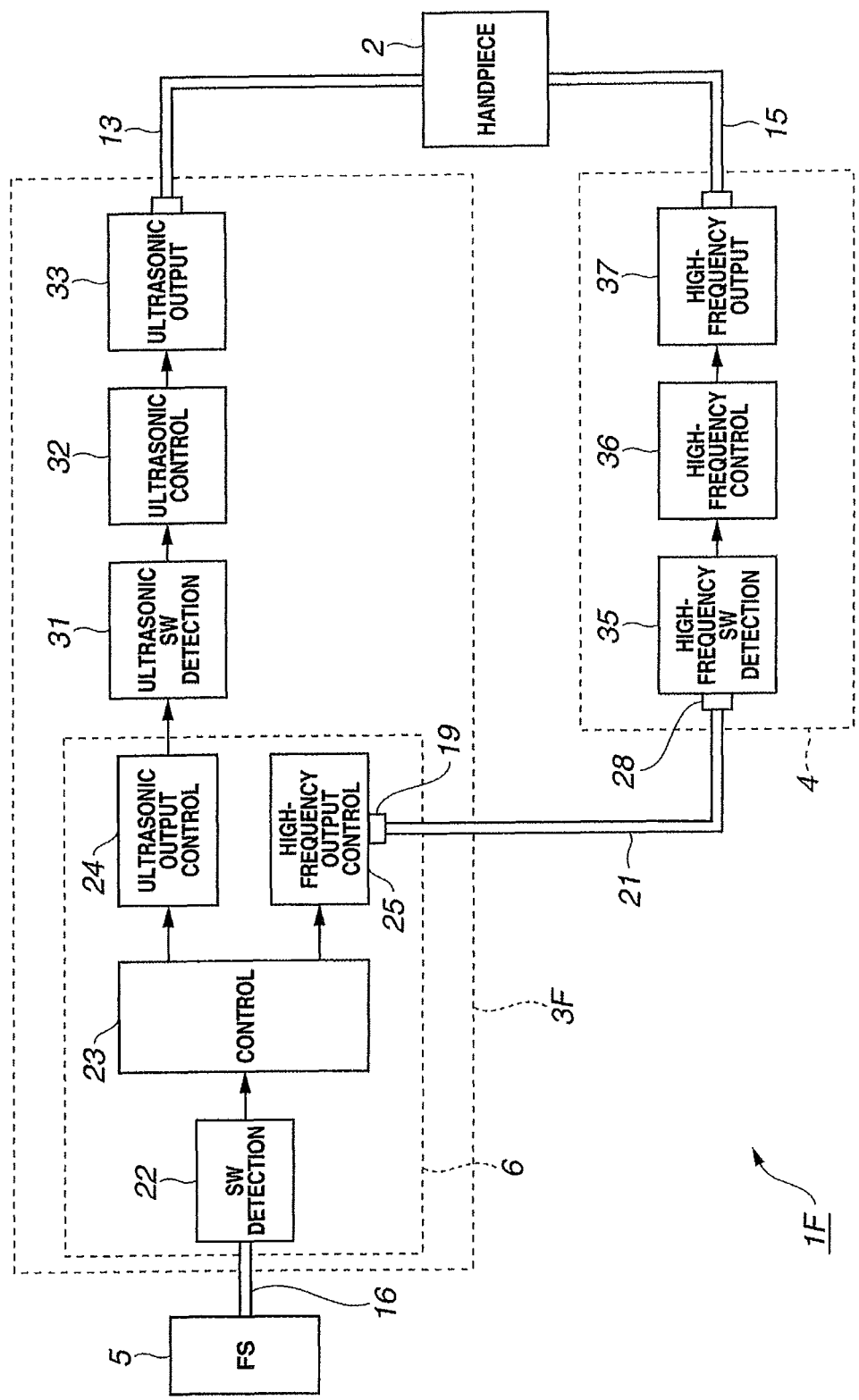
FIG. 26 is a block diagram illustrating the internal structure of the ultrasonic-surgical and electrosurgical system according to the sixth embodiment.

FIG. 26 illustrates more detailed structure of FIG. 25.

The relay device 6 to which the footswitch 5 is connected through the footswitch cable 16 includes the switch detection unit 22, the control unit 23, the ultrasonic output control unit 24, and the high-frequency output control unit 25.

The output terminal of the ultrasonic output control unit 24 is connected to the ultrasonic switch detection unit 31 included in the ultrasonic surgical device 3F. The ultrasonic surgical device 3F includes the ultrasonic control unit 32 and the ultrasonic output unit 33, in addition to the ultrasonic switch detection unit 31.

In addition, the electrosurgical device 4, which is connected to the high-frequency connector 19 of the high-frequency output control unit 25 in the relay device 6 through the electrosurgical device connecting cable 21, includes the high-frequency switch detection unit 35, the high-frequency control unit 36, and the high-frequency output unit 37.

The ultrasonic-surgical and electrosurgical system of the present embodiment differs from the ultrasonic-surgical and electrosurgical system 1 in FIG. 2 in that the relay device 6 is provided in the ultrasonic surgical device 3.

In the present embodiment, the ultrasonic surgical device 3F which has the relay device 6 built in and the electrosurgical device 4 are used, so that the system of the present embodiment can be used in the same manner as that of the first embodiment.

In this case, the ultrasonic surgical device 3F has the relay device 6 built in. Therefore, the present embodiment has the merit to cause the system to act in the same manner as the ultrasonic-surgical and electrosurgical system 1 according to the first embodiment, without the need for connecting the relay device 6 and the ultrasonic surgical device 3 with the ultrasonic surgical device connecting cable 20 as in the first embodiment.

Accordingly, the present embodiment has the following effect. In the ultrasonic-surgical and electrosurgical system 1F according to the present embodiment, the operator can control the outputs of both of the ultrasonic surgical device 3F and the electrosurgical device 4 by operating only the single footswitch 5 connected to the relay device 6.

In other words, the operator can control outputs of both of the devices 3F and 4 by operating only the single common footswitch 5 instead of the two footswitches 94 and 95 which are provided independently of each other in the system 91 in the prior example shown in FIG. 24, which results in improvement of the operability. Therefore, the operator can easily manipulate the switch during a treatment.

In addition, since the number of footswitches to be operated is reduced, an operating room becomes clear. Specifically, the number of cables arranged around the operator's feet can also be reduced.

Furthermore, in the ultrasonic-surgical and electrosurgical system 1F of the present embodiment, switch-on/off signals, which have compatibility with the signals when the existing footswitches are directly operated, are outputted from the relay device 6.

Therefore, as shown in FIG. 24, the existing electrosurgical device 4 to which the footswitch 95 dedicated to the electrosurgical device can be used.

In addition, according to the present embodiment, signal transmission and reception between the relay device 6 and the electrosurgical device 4 are performed using the photocouplers. Accordingly, ground isolation between the ultrasonic surgical device 3F and the electrosurgical device 4 can be provided, so that the devices can be sufficiently kept electrically isolated from each other.

Although the present embodiment has been described by using the example in which the relay device 6 is built in the ultrasonic surgical device 3 in the first embodiment, the present embodiment can be applied also to other embodiments 2 to 5 in the same manner as described above.

In addition, although the present embodiment has been described by using the example in which the relay device 6 is built in the ultrasonic surgical device 3, the relay device 6 may be built in the electrosurgical device 4 as in the following seventh embodiment.

Seventh Embodiment

Figure 27:
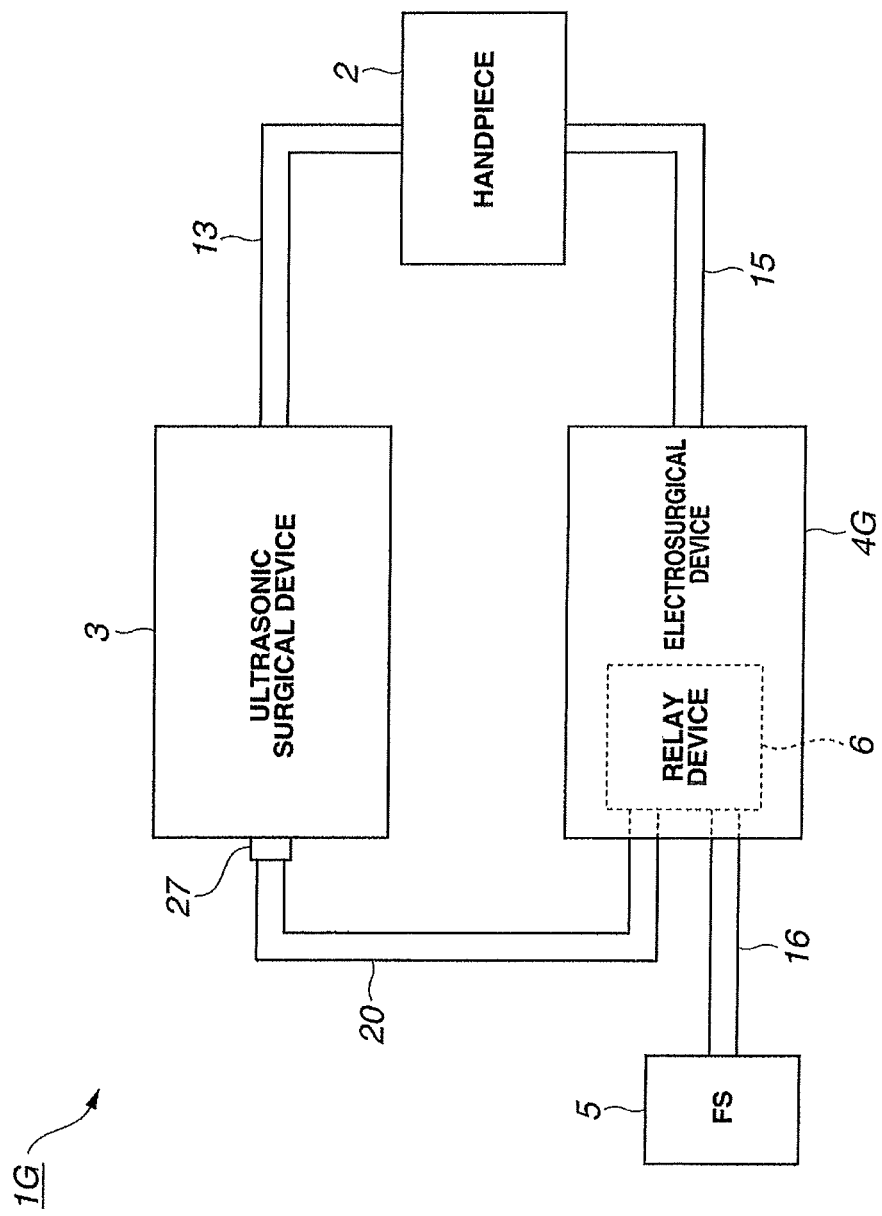
FIG. 27 is a block diagram illustrating the whole structure of an ultrasonic-surgical and electrosurgical system according to a seventh embodiment of the present invention.

Next, the seventh embodiment of the present invention will be described with reference to FIGS. 27 and 28. FIG. 27 illustrates the structure of the ultrasonic-surgical and electrosurgical system 1G according to the seventh embodiment of the present invention.

The ultrasonic-surgical and electrosurgical system 1G shown in FIG. 27 differs from the ultrasonic-surgical and electrosurgical system 1 according to the first embodiment shown in FIG. 1 in that the relay device 6 is built in the electrosurgical device 4, for example.

The ultrasonic-surgical and electrosurgical system 1G includes the handpiece 2, the ultrasonic surgical device 3, an electrosurgical device 4G in which the relay device 6 controlling output modes and output timings is built, and the footswitch 5 connected to the electrosurgical device 4G.

The ultrasonic handpiece cable 13 of the handpiece 2 is connected to the output connector of the ultrasonic surgical device 3, and the high-frequency handpiece cable 15 is connected to an output connector of the electrosurgical device 4G.

In addition, the footswitch 5 is connected to the relay device 6 disposed inside of the electrosurgical device 4G through the footswitch cable 16.

In this case, the footswitch cable 16 may include a footswitch cable unit which connects the footswitch 5 and the electrosurgical device 4G, and a connecting cable unit which is connected to one end of the footswitch cable unit to connect the footswitch cable unit to the relay device 6 disposed in the electrosurgical device 4G.

In addition, the relay device 6 disposed inside of the electrosurgical device 4G is connected to the ultrasonic connector 27 of the ultrasonic surgical device 3 through the ultrasonic surgical device connecting cable 20. Also in this case, the ultrasonic surgical device connecting cable 20 may include an ultrasonic surgical device connecting cable unit which connects the ultrasonic connector 27 of the ultrasonic surgical device 3 and the electrosurgical device 4G, and a connecting cable unit which is connected to one end of the ultrasonic surgical device connecting cable unit to connect the ultrasonic surgical device connecting cable unit to the relay device 6 disposed inside of the electrosurgical device 4G.

Figure 28:
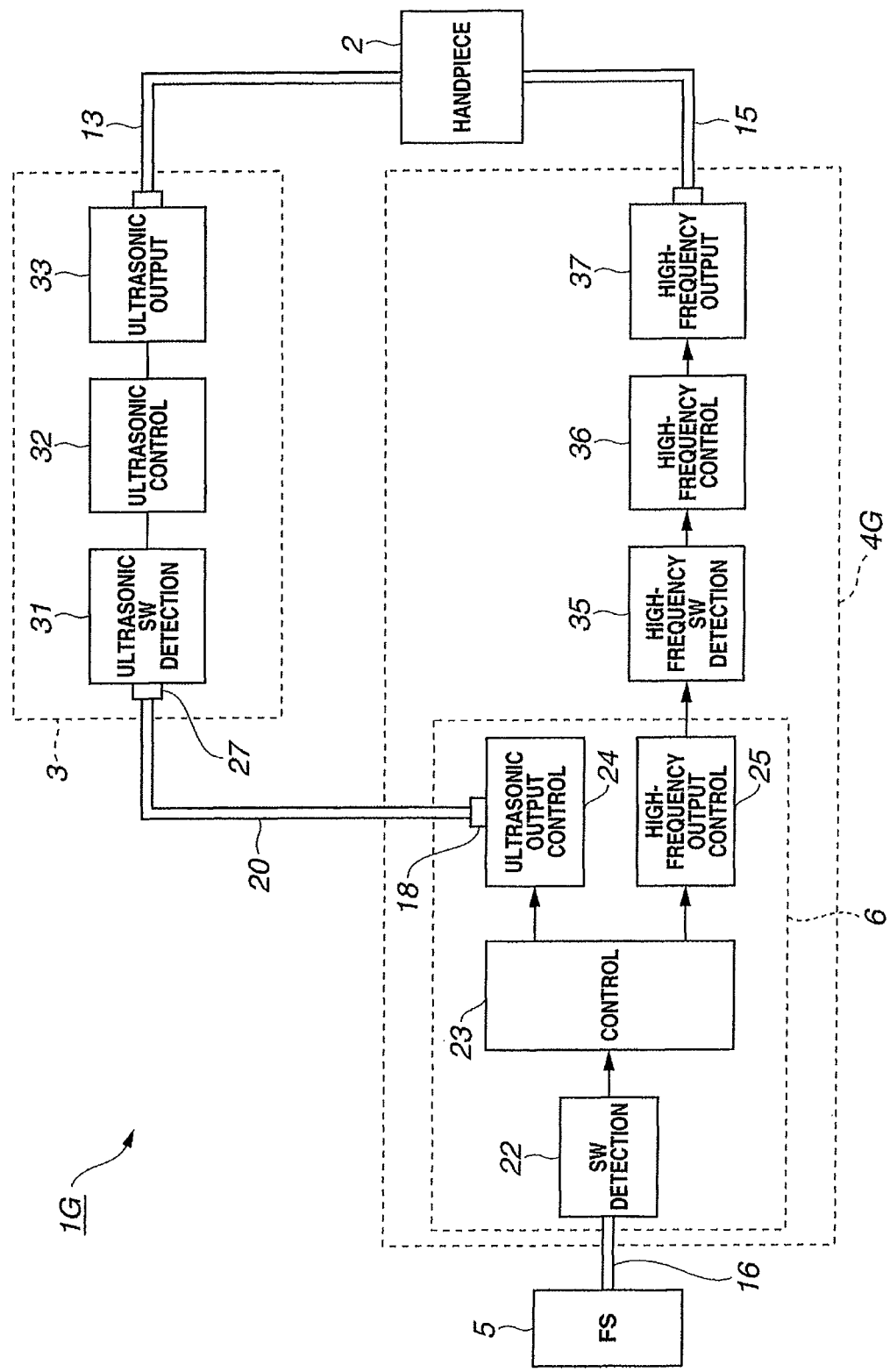
FIG. 28 is a block diagram illustrating the internal structure of the ultrasonic-surgical and electrosurgical system according to the seventh embodiment.

FIG. 28 illustrates more detailed structure of FIG. 27.

The relay device 6 to which the footswitch 5 is connected through the footswitch cable 16 includes the switch detection unit 22, the control unit 23, the ultrasonic output control unit 24, and the high-frequency output control unit 25.

The high-frequency output control unit 25 is connected to the high-frequency switch detection unit 35 included in the electrosurgical device 4G. The electrosurgical device 4G includes the high-frequency control unit 36 and the high-frequency output unit 37, in addition to the high-frequency switch detection unit 35.

The ultrasonic surgical device 3, which is connected to the ultrasonic connector 18 of the ultrasonic output control unit 24 in the relay device 6 through the ultrasonic surgical device connecting cable 20, includes the ultrasonic switch detection unit 31, the ultrasonic control unit 32, and the ultrasonic output unit 33.

The ultrasonic-surgical and electrosurgical system of the present embodiment differs from the ultrasonic-surgical and electrosurgical system 1 in FIG. 2 in that the relay device 6 is provided in the electrosurgical device 4.

In the present embodiment, the electrosurgical device 4G which has the relay device 6 built in and the ultrasonic surgical device 3 are used, so that the system of the present embodiment can be used in the same manner as that of the first embodiment.

In this case, the electrosurgical device 4G has the relay device 6 built in. Therefore, the present embodiment has the merit to cause the system to act in the same manner as the ultrasonic-surgical and electrosurgical system 1 according to the first embodiment, without the need for connecting the relay device 6 and the electrosurgical device 4 with the electrosurgical device connecting cable 21 as in the first embodiment.

The present embodiment also has the following effect similar to that in the sixth embodiment. In the ultrasonic-surgical and electrosurgical system 1G according to the present embodiment, the operator can control the outputs of both of the ultrasonic surgical device 3 and the electrosurgical device 4G by operating only the single footswitch 5 connected to the relay device 6.

That is, the operator can control the outputs of both of the devices 3 and 4G by operating only the single common footswitch 5 instead of two footswitches 94 and 95 which are provided independently of each other in the system 91 in the prior example shown in FIG. 24, which results in improvement of the operability. Therefore, the operator can easily manipulate the switch during a treatment.

In addition, since the number of footswitches to be operated is reduced, an operating room becomes clear. Specifically, the number of cables arranged around the operator's feet can also be reduced.

Furthermore, in the ultrasonic-surgical and electrosurgical system 1G of the present embodiment, the switch-on/off signals, which have compatibility with the signals when the existing footswitches are directly operated, are outputted from the relay device 6.

Therefore, as shown in FIG. 24, the existing ultrasonic surgical device 3 to which the footswitch 94 dedicated to the ultrasonic surgical device can be used.

In addition, according to the present embodiment, signal transmission and reception between the relay device 6 and the ultrasonic surgical device 3 are performed using the photocouplers. Accordingly, ground isolation between the ultrasonic surgical device 3 and the electrosurgical device 4G can be provided, so that the devices can be sufficiently kept electrically isolated from each other.

In addition, although the present embodiment has been described by using the example in which the relay device 6 is built in the electrosurgical device 4 in the first embodiment, the present embodiment can be applied also to other embodiments 2 to 5 in the same manner as described above.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgical controller for controlling a treatment instrument, the treatment instrument being configured to perform a first treatment and a second treatment, the first treatment being based on a first surgical energy, and the second treatment being based on a second surgical energy different from the first surgical energy, the surgical controller comprising one or more processors configured to:

detect whether a switch is actuated;
control a first surgical energy source to actuate the treatment instrument to perform the first treatment based on the first surgical energy in response to detecting that the switch is actuated;
detect whether a parameter reaches a predetermined value during actuation of the treatment instrument to perform the first treatment, the predetermined value indicating that an output timing of the first surgical energy is reached; and
control a second surgical energy source to actuate the treatment instrument to perform the second treatment based on the second surgical energy in response to detecting that the parameter reached the predetermined value.

2. The surgical controller according to claim 1,
wherein the one or more processors are configured to control the first surgical energy source to perform the first treatment based on an ultrasonic vibration.

3. The surgical controller according to claim 2,
wherein the one or more processors are configured to control the second surgical energy source to perform the second treatment based on a high-frequency current.

4. The surgical controller according to claim 1,
wherein the one or more processors are configured to detect a type of the treatment instrument prior to detecting whether the switch is actuated.

5. The surgical controller according to claim 4,
wherein the one or more processors are configured to control an output timing and an output mode of each of the first surgical energy and the second surgical energy on the basis of the type of the treatment instrument detected.

6. The surgical controller according to claim 1,
wherein the one or more processors are configured to control the second surgical energy source to intermittently actuate the treatment instrument to perform the second treatment.

7. A method for controlling a treatment instrument to perform a treatment, the treatment instrument being configured to perform a first treatment and a second treatment, the first treatment being based on a first surgical energy, and the second treatment being based on a second surgical energy different from the first surgical energy, the method comprising:

detecting whether a switch is actuated;
controlling a first surgical energy source to actuate the treatment instrument to perform the first treatment based on the first surgical energy in response to detecting that the switch is actuated;
detecting whether a parameter reaches a predetermined value during actuation of the treatment instrument to perform the first treatment, the predetermined value indicating that an output timing of the first surgical energy is reached; and
controlling a second surgical energy source to actuate the treatment instrument to perform the second treatment based on the second surgical energy in response to detecting that the parameter reached the predetermined value.

8. The method according to claim 7,
wherein the controlling the first surgical energy source to actuate the treatment instrument to perform the first treatment based on the first surgical energy in response to detecting that the switch is actuated comprises:
controlling the first surgical energy source to actuate the treatment instrument to perform the first treatment based on an ultrasonic vibration in response to detecting that the switch is actuated.

9. A surgical apparatus comprising:
a treatment instrument configured to perform a first treatment and a second treatment, the first treatment being based on a first surgical energy, and the second treatment being based on a second surgical energy different from the first surgical energy; and
a surgical controller comprising one or more processors configured to:
  detect whether a switch is actuated;
  control a first surgical energy source to actuate the treatment instrument to perform the first treatment based on the first surgical energy in response to detecting that the switch is actuated;
  detect whether a parameter reaches a predetermined value during actuation of the treatment instrument to perform the first treatment, the predetermined value indicating that an output timing of the first surgical energy is reached; and
  control a second surgical energy source to actuate the treatment instrument to perform the second treatment based on the second surgical energy in response to detecting that the parameter reached the predetermined value.

10. A surgical apparatus comprising:
a treatment instrument configured to perform a first treatment and a second treatment, the first treatment being based on a first surgical energy, and the second treatment being based on a second surgical energy different from the first surgical energy;
a switch; and
a circuit configured to form a first electric connection between the switch and a surgical controller, a second electric connection between the treatment instrument and the surgical controller, and a third electric connection between the treatment instrument and the surgical controller,
wherein the circuit is configured to:
  communicate with the surgical controller through the first electric connection in response to an occurrence that the switch is actuated;
  receive a first electric power from a first surgical energy source through the second electric connection, wherein the first electric power is configured to actuate the treatment instrument to perform the first treatment based on the first surgical energy in response to the occurrence; and
  subsequent to receiving the first electric power, receive a second electric power from a second surgical energy source through the third electric connection, wherein the second electric power is configured to actuate the treatment instrument to perform the second treatment based on the second surgical energy in response to another occurrence that a parameter reached a predetermined value during actuation of the treatment instrument to perform the first treatment, the predetermined value indicating that an output timing of the first surgical energy is reached.

* * * * *